US010238500B2

(12) United States Patent
Rogers et al.

(10) Patent No.: US 10,238,500 B2
(45) Date of Patent: Mar. 26, 2019

(54) INTERVERTEBRAL DISC

(71) Applicant: DePuy Synthes Products, Inc., Raynham, MA (US)

(72) Inventors: Christopher Rogers, Allendale, NJ (US); Andrew Dooris, Raynham, MA (US); Patrick J. Fatyol, Whitman, MA (US); Mark Lionetto, Norton, MA (US); Ronald J. Naughton, Pleasanton, CA (US); John Riley Hawkins, Cumberland, RI (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/942,246

(22) Filed: Nov. 16, 2015

(65) Prior Publication Data

US 2016/0074170 A1 Mar. 17, 2016

Related U.S. Application Data

(62) Division of application No. 12/395,606, filed on Feb. 27, 2009, now Pat. No. 9,993,349, which is a division
(Continued)

(51) Int. Cl.
*A61F 2/44* (2006.01)
*A61F 2/08* (2006.01)
(Continued)

(52) U.S. Cl.
CPC ............ *A61F 2/442* (2013.01); *A61F 2/4425* (2013.01); *A61F 2/08* (2013.01); *A61F 2/30724* (2013.01);
(Continued)

(58) Field of Classification Search
CPC .......... A61L 27/28; A61F 2310/00616; A61F 2/4425; A61F 2002/443; A61F 2/442
See application file for complete search history.

(56) References Cited

U.S. PATENT DOCUMENTS

| | | |
|---|---|---|
| 2,115,250 A | 4/1938 | Bruson et al. |
| 2,170,111 A | 8/1939 | Bruson et al. |

(Continued)

FOREIGN PATENT DOCUMENTS

| | | |
|---|---|---|
| CN | 101909548 A | 12/2010 |
| DE | 2804936 | 8/1979 |

(Continued)

OTHER PUBLICATIONS

Harsha et al., Tribo performance of polyaryletherketone composites, Polymer Testing (21) (2002) pp. 697-709.*
(Continued)

*Primary Examiner* — Anu Ramana
(74) *Attorney, Agent, or Firm* — Baker & Hostetler LLP

(57) ABSTRACT

This invention relates to an intervertebral motion disc having two motion surfaces and. wherein the radius of the upper articulation surface of the core member is greater than the radius of the lower articulation surface of the core member, and wherein the first articulation surface of the core member is spherical and the second articulation surface of the core member is curved and non-spherical.

11 Claims, 23 Drawing Sheets

Related U.S. Application Data of application No. 10/465,277, filed on Jun. 19, 2003, now Pat. No. 7,517,363.

(60) Provisional application No. 60/391,845, filed on Jun. 27, 2002.

(51) Int. Cl.
    A61F 2/30    (2006.01)
    A61F 2/46    (2006.01)
    A61F 2/28    (2006.01)

(52) U.S. Cl.
    CPC ......... A61F 2/30767 (2013.01); A61F 2/4611 (2013.01); A61F 2002/2817 (2013.01); A61F 2002/302 (2013.01); A61F 2002/304 (2013.01); A61F 2002/305 (2013.01); A61F 2002/3008 (2013.01); A61F 2002/30062 (2013.01); A61F 2002/3082 (2013.01); A61F 2002/30092 (2013.01); A61F 2002/30224 (2013.01); A61F 2002/30232 (2013.01); A61F 2002/30245 (2013.01); A61F 2002/30247 (2013.01); A61F 2002/30253 (2013.01); A61F 2002/30327 (2013.01); A61F 2002/30369 (2013.01); A61F 2002/30383 (2013.01); A61F 2002/30387 (2013.01); A61F 2002/30433 (2013.01); A61F 2002/30462 (2013.01); A61F 2002/30466 (2013.01); A61F 2002/30481 (2013.01); A61F 2002/30495 (2013.01); A61F 2002/30497 (2013.01); A61F 2002/30515 (2013.01); A61F 2002/30528 (2013.01); A61F 2002/30563 (2013.01); A61F 2002/30565 (2013.01); A61F 2002/30566 (2013.01); A61F 2002/30578 (2013.01); A61F 2002/30604 (2013.01); A61F 2002/30649 (2013.01); A61F 2002/30662 (2013.01); A61F 2002/30733 (2013.01); A61F 2002/30838 (2013.01); A61F 2002/30841 (2013.01); A61F 2002/30843 (2013.01); A61F 2002/30878 (2013.01); A61F 2002/30883 (2013.01); A61F 2002/30892 (2013.01); A61F 2002/30939 (2013.01); A61F 2002/443 (2013.01); A61F 2210/0004 (2013.01); A61F 2210/0014 (2013.01); A61F 2220/0025 (2013.01); A61F 2220/0033 (2013.01); A61F 2220/0041 (2013.01); A61F 2220/0075 (2013.01); A61F 2230/0065 (2013.01); A61F 2230/0069 (2013.01); A61F 2230/0071 (2013.01); A61F 2230/0076 (2013.01); A61F 2250/0039 (2013.01); A61F 2250/0098 (2013.01); A61F 2310/00017 (2013.01); A61F 2310/00023 (2013.01); A61F 2310/00029 (2013.01); A61F 2310/0058 (2013.01); A61F 2310/00203 (2013.01); A61F 2310/00239 (2013.01); A61F 2310/00796 (2013.01)

(56) References Cited

U.S. PATENT DOCUMENTS

| | | | |
|---|---|---|---|
| 2,229,024 A | 1/1941 | Bruson et al. | |
| 2,706,701 A | 4/1955 | Hans et al. | |
| 2,710,277 A | 6/1955 | Shelanski et al. | |
| 2,826,532 A | 3/1958 | Hosmer et al. | |
| 2,900,305 A | 8/1959 | Sidney et al. | |
| 2,977,315 A | 3/1961 | Scheib et al. | |
| 3,228,828 A | 1/1966 | Romano et al. | |
| 3,717,655 A | 2/1973 | Godefroi et al. | |
| 3,867,728 A | 2/1975 | Stubstad et al. | |
| 4,349,921 A | 9/1982 | Kuntz | |
| 4,351,069 A * | 9/1982 | Ballintyn | A61C 8/0013 156/77 |
| 4,352,883 A | 10/1982 | Lim | |
| 4,440,921 A | 4/1984 | Allcock et al. | |
| 4,495,174 A | 1/1985 | Allcock et al. | |
| 4,542,539 A * | 9/1985 | Rowe, Jr. | A61F 2/30767 623/23.57 |
| 4,645,503 A | 2/1987 | Lin et al. | |
| 4,651,717 A | 3/1987 | Jakubczak | |
| 4,743,256 A | 5/1988 | Brantigan | |
| 4,759,766 A * | 7/1988 | Buettner-Janz | A61F 2/4425 623/17.15 |
| 4,772,287 A | 9/1988 | Ray et al. | |
| 4,863,476 A | 9/1989 | Shepperd | |
| 4,870,153 A * | 9/1989 | Matzner | C08G 61/127 528/125 |
| 4,871,366 A | 10/1989 | von Recum et al. | |
| 4,878,915 A | 11/1989 | Brantigan | |
| 4,880,622 A | 11/1989 | Allcock et al. | |
| 4,911,718 A | 3/1990 | Lee et al. | |
| 4,932,969 A | 6/1990 | Frey et al. | |
| 4,946,378 A | 8/1990 | Hirayama et al. | |
| 5,030,233 A | 7/1991 | Ducheyne | |
| 5,059,193 A | 10/1991 | Kuslich | |
| 5,071,437 A * | 12/1991 | Steffee | A61F 2/442 606/247 |
| 5,133,755 A | 7/1992 | Brekke | |
| 5,134,477 A | 7/1992 | Knauer et al. | |
| 5,192,327 A | 3/1993 | Brantigan | |
| 5,290,312 A | 3/1994 | Kojimoto et al. | |
| 5,306,307 A * | 4/1994 | Senter | A61F 2/442 623/17.16 |
| 5,306,308 A | 4/1994 | Gross et al. | |
| 5,314,477 A | 5/1994 | Marnay | |
| 5,344,252 A | 9/1994 | Kakimoto | |
| 5,370,697 A | 12/1994 | Baumgartner | |
| 5,372,660 A | 12/1994 | Davidson et al. | |
| 5,374,267 A | 12/1994 | Siegal | |
| 5,390,683 A | 2/1995 | Pisharodi | |
| 5,397,364 A | 3/1995 | Kozak et al. | |
| 5,401,269 A | 3/1995 | Buttner-Janz et al. | |
| 5,410,016 A | 4/1995 | Hubbell et al. | |
| 5,425,773 A * | 6/1995 | Boyd | A61F 2/4425 623/17.15 |
| 5,443,514 A | 8/1995 | Steffee | |
| 5,458,641 A | 10/1995 | Ramirez | |
| 5,458,643 A | 10/1995 | Oka et al. | |
| 5,507,816 A | 4/1996 | Bullivant | |
| 5,514,180 A | 5/1996 | Heggeness et al. | |
| 5,522,895 A | 6/1996 | Mikos | |
| 5,522,899 A | 6/1996 | Michelson | |
| 5,534,029 A | 7/1996 | Shima | |
| 5,534,030 A | 7/1996 | Navarro et al. | |
| 5,549,679 A | 8/1996 | Kuslich | |
| 5,554,191 A | 9/1996 | Lahille et al. | |
| 5,556,431 A | 9/1996 | Buttner-Janz | |
| 5,562,736 A | 10/1996 | Ray et al. | |
| 5,562,738 A | 10/1996 | Boyd et al. | |
| 5,609,635 A | 3/1997 | Michelson | |
| 5,645,596 A | 7/1997 | Kim et al. | |
| 5,653,763 A | 8/1997 | Errico | |
| 5,658,335 A | 8/1997 | Allen | |
| 5,665,122 A | 9/1997 | Kambin | |
| 5,674,296 A | 10/1997 | Bryan et al. | |
| 5,676,701 A | 10/1997 | Yuan et al. | |
| 5,679,723 A | 10/1997 | Cooper et al. | |
| 5,683,465 A | 11/1997 | Shinn et al. | |
| 5,697,977 A | 12/1997 | Pisharodi | |
| 5,702,449 A | 12/1997 | McKay | |
| 5,702,450 A | 12/1997 | Bisserie | |
| 5,716,415 A | 2/1998 | Steffee | |
| 5,755,798 A | 5/1998 | Papavero et al. | |
| 5,772,661 A | 6/1998 | Michelson | |
| 5,782,832 A | 7/1998 | Larsen et al. | |
| 5,800,549 A | 9/1998 | Bao et al. | |
| 5,807,327 A | 9/1998 | Green et al. | |
| 5,824,084 A | 10/1998 | Muschler | |

(56) References Cited

U.S. PATENT DOCUMENTS

| | | |
|---|---|---|
| 5,824,094 A | 10/1998 | Serhan et al. |
| 5,833,657 A | 11/1998 | Reinhardt et al. |
| 5,837,752 A | 11/1998 | Shastri et al. |
| 5,860,973 A | 1/1999 | Michelson |
| 5,865,846 A | 2/1999 | Bryan et al. |
| 5,865,848 A | 2/1999 | Baker |
| 5,888,220 A | 3/1999 | Felt et al. |
| 5,888,224 A | 3/1999 | Beckers et al. |
| 5,888,226 A | 3/1999 | Rogozinski |
| 5,888,227 A | 3/1999 | Cottle |
| 5,893,889 A | 4/1999 | Harrington |
| 5,893,890 A | 4/1999 | Pisharodi |
| 5,895,428 A | 4/1999 | Berry |
| 5,972,385 A | 10/1999 | Liu et al. |
| 5,980,522 A | 11/1999 | Koros et al. |
| 5,985,307 A | 11/1999 | Hanson et al. |
| 5,989,291 A | 11/1999 | Ralph et al. |
| 6,019,792 A | 2/2000 | Cauthen |
| 6,022,350 A | 2/2000 | Ganem |
| 6,039,761 A | 3/2000 | Li |
| 6,039,763 A | 3/2000 | Shelokov |
| 6,045,579 A | 4/2000 | Hochshuler et al. |
| 6,063,121 A | 5/2000 | Xavier et al. |
| 6,071,982 A | 6/2000 | Wise et al. |
| 6,099,531 A | 8/2000 | Bonutti |
| 6,102,950 A | 8/2000 | Vaccaro |
| 6,106,557 A | 8/2000 | Robioneck et al. |
| 6,113,624 A | 9/2000 | Bezwada et al. |
| 6,113,637 A | 9/2000 | Gill et al. |
| 6,113,638 A | 9/2000 | Williams et al. |
| 6,117,174 A | 9/2000 | Nolan |
| 6,126,689 A | 10/2000 | Brett |
| 6,127,597 A | 10/2000 | Beyar et al. |
| 6,129,763 A | 10/2000 | Chauvin et al. |
| 6,136,031 A | 10/2000 | Middleton |
| 6,139,579 A | 10/2000 | Steffee et al. |
| 6,146,387 A | 11/2000 | Trott et al. |
| 6,146,421 A | 11/2000 | Gordon et al. |
| 6,147,135 A | 11/2000 | Yuan et al. |
| 6,162,252 A | 12/2000 | Kuras et al. |
| 6,165,486 A | 12/2000 | Marra et al. |
| 6,171,610 B1 | 1/2001 | Vacanti et al. |
| 6,176,882 B1 | 1/2001 | Biedermann et al. |
| 6,179,794 B1 | 1/2001 | Burras |
| 6,179,873 B1 | 1/2001 | Zientek |
| 6,183,517 B1 | 2/2001 | Suddaby |
| 6,187,043 B1 | 2/2001 | Ledergerber |
| 6,187,048 B1 | 2/2001 | Milner et al. |
| 6,193,757 B1 | 2/2001 | Foley et al. |
| 6,197,065 B1 * | 3/2001 | Martin .............. A61B 17/164 623/23.17 |
| 6,197,325 B1 | 3/2001 | MacPhee et al. |
| 6,203,565 B1 | 3/2001 | Bonutti et al. |
| 6,214,368 B1 | 4/2001 | Lee et al. |
| 6,217,579 B1 | 4/2001 | Koros |
| 6,224,631 B1 | 5/2001 | Kohrs |
| 6,224,894 B1 | 5/2001 | Jamiolkowski et al. |
| 6,241,769 B1 * | 6/2001 | Nicholson .......... A61B 17/1604 623/17.11 |
| 6,248,131 B1 | 6/2001 | Felt et al. |
| 6,264,695 B1 | 7/2001 | Stoy |
| 6,277,149 B1 | 8/2001 | Boyle et al. |
| 6,280,474 B1 | 8/2001 | Cassidy et al. |
| 6,296,647 B1 | 10/2001 | Robioneck et al. |
| 6,302,914 B1 | 10/2001 | Michelson |
| 6,306,177 B1 | 10/2001 | Felt et al. |
| 6,331,312 B1 | 12/2001 | Lee et al. |
| 6,332,894 B1 | 12/2001 | Stalcup et al. |
| 6,332,895 B1 | 12/2001 | Suddaby |
| 6,368,325 B1 | 4/2002 | McKinley et al. |
| 6,368,350 B1 | 4/2002 | Erickson et al. |
| 6,368,351 B1 | 4/2002 | Glenn et al. |
| 6,375,681 B1 | 4/2002 | Truscott |
| 6,375,682 B1 | 4/2002 | Fleischmann et al. |
| 6,387,130 B1 | 5/2002 | Stone et al. |
| 6,409,766 B1 | 6/2002 | Brett |
| 6,413,278 B1 | 7/2002 | Marchosky |
| 6,416,551 B1 | 7/2002 | Keller |
| 6,419,705 B1 | 7/2002 | Erickson |
| 6,419,706 B1 | 7/2002 | Graf |
| 6,436,140 B1 | 8/2002 | Liu et al. |
| 6,443,989 B1 | 9/2002 | Jackson |
| 6,454,806 B1 | 9/2002 | Cohen et al. |
| 6,454,807 B1 | 9/2002 | Jackson |
| 6,468,310 B1 | 10/2002 | Ralph et al. |
| 6,488,710 B2 | 12/2002 | Besselink |
| 6,491,724 B1 | 12/2002 | Ferree |
| 6,494,883 B1 | 12/2002 | Ferree |
| 6,517,580 B1 | 2/2003 | Ramadan et al. |
| 6,527,804 B1 | 3/2003 | Gauchet et al. |
| 6,533,818 B1 | 3/2003 | Weber et al. |
| 6,547,823 B2 | 4/2003 | Scarborough et al. |
| 6,558,424 B2 | 5/2003 | Thalgott |
| 6,562,072 B1 | 5/2003 | Fuss et al. |
| 6,562,074 B2 | 5/2003 | Gerbec et al. |
| 6,579,320 B1 | 6/2003 | Gauchet et al. |
| 6,582,431 B1 | 6/2003 | Ray |
| 6,582,466 B1 | 6/2003 | Gauchet |
| 6,582,468 B1 | 6/2003 | Gauchet |
| 6,592,624 B1 | 7/2003 | Fraser et al. |
| 6,592,625 B2 | 7/2003 | Cauthen |
| 6,595,998 B2 | 7/2003 | Johnson et al. |
| 6,607,558 B2 | 8/2003 | Kuras |
| 6,610,094 B2 | 8/2003 | Husson |
| 6,626,943 B2 | 9/2003 | Eberlein et al. |
| 6,632,235 B2 | 10/2003 | Weikel et al. |
| 6,641,614 B1 | 11/2003 | Wagner et al. |
| 6,645,248 B2 | 11/2003 | Casutt |
| 6,648,917 B2 | 11/2003 | Gerbec et al. |
| 6,669,732 B2 | 12/2003 | Serhan et al. |
| 6,676,665 B2 | 1/2004 | Foley et al. |
| 6,682,562 B2 | 1/2004 | Viart et al. |
| 6,685,742 B1 | 2/2004 | Jackson |
| 6,706,070 B1 | 3/2004 | Wagner et al. |
| 6,719,796 B2 | 4/2004 | Cohen et al. |
| 6,723,126 B1 | 4/2004 | Berry |
| 6,723,127 B2 | 4/2004 | Ralph et al. |
| 6,733,532 B1 | 5/2004 | Gauchet et al. |
| 6,733,535 B2 | 5/2004 | Michelson |
| 6,740,117 B2 | 5/2004 | Ralph et al. |
| 6,743,255 B2 | 6/2004 | Ferree |
| 6,758,861 B2 | 7/2004 | Ralph et al. |
| 6,793,678 B2 | 9/2004 | Hawkins |
| 6,805,697 B1 | 10/2004 | Helm et al. |
| 6,805,714 B2 | 10/2004 | Sutcliffe |
| 6,835,208 B2 | 12/2004 | Marchosky |
| 6,855,167 B2 | 2/2005 | Shimp |
| 6,863,673 B2 | 3/2005 | Gerbec et al. |
| 6,881,229 B2 | 4/2005 | Khandkar et al. |
| 6,893,464 B2 | 5/2005 | Kiester |
| 6,936,071 B1 | 8/2005 | Marnay et al. |
| 6,953,477 B2 | 10/2005 | Berry |
| 6,955,691 B2 | 10/2005 | Chae et al. |
| 6,964,686 B2 | 11/2005 | Gordon |
| 6,969,404 B2 | 11/2005 | Ferree |
| 6,969,405 B2 | 11/2005 | Suddaby |
| 6,979,352 B2 | 12/2005 | Reynolds |
| 6,979,353 B2 | 12/2005 | Bresina |
| 7,018,412 B2 | 3/2006 | Ferreira et al. |
| 7,018,416 B2 | 3/2006 | Hanson et al. |
| 7,025,787 B2 | 4/2006 | Bryan et al. |
| 7,037,339 B2 | 5/2006 | Houfburg et al. |
| 7,083,650 B2 | 8/2006 | Moskowitz et al. |
| 7,094,257 B2 | 8/2006 | Mujwid et al. |
| 7,156,876 B2 | 1/2007 | Moumene et al. |
| 7,211,112 B2 | 5/2007 | Baynham et al. |
| 7,217,293 B2 | 5/2007 | Branch |
| 7,220,280 B2 | 5/2007 | Kast et al. |
| 7,223,292 B2 | 5/2007 | Messerli et al. |
| 7,226,483 B2 | 6/2007 | Gerber et al. |
| 7,235,101 B2 | 6/2007 | Berry et al. |
| 7,291,173 B2 | 11/2007 | Richelsoph et al. |
| 7,326,248 B2 | 2/2008 | Michelson |
| 7,442,211 B2 | 10/2008 | de Villiers et al. |

(56) References Cited

U.S. PATENT DOCUMENTS

| | | | |
|---|---|---|---|
| 7,500,991 | B2 | 3/2009 | Bartish, Jr. et al. |
| 7,503,920 | B2 | 3/2009 | Siegal |
| 7,503,933 | B2 | 3/2009 | Michelson |
| 7,507,241 | B2 | 3/2009 | Levy et al. |
| 7,517,363 | B2 | 4/2009 | Rogers et al. |
| 7,569,074 | B2 | 8/2009 | Eiserman et al. |
| 7,618,458 | B2 | 11/2009 | Biedermann et al. |
| 7,621,950 | B1 | 11/2009 | Globerman et al. |
| 7,621,960 | B2 | 11/2009 | Boyd et al. |
| 7,641,692 | B2 | 1/2010 | Bryan et al. |
| 7,655,010 | B2 | 2/2010 | Serhan et al. |
| 7,666,266 | B2 | 2/2010 | Izawa et al. |
| 7,670,374 | B2 | 3/2010 | Schaller |
| 7,691,147 | B2 | 4/2010 | Gutlin et al. |
| 7,703,727 | B2 | 4/2010 | Selness |
| 7,722,612 | B2 | 5/2010 | Sala et al. |
| 7,722,674 | B1 | 5/2010 | Grotz |
| 7,749,270 | B2 | 7/2010 | Peterman |
| 7,771,473 | B2 | 8/2010 | Thramann |
| 7,785,368 | B2 | 8/2010 | Schaller |
| 7,789,914 | B2 | 9/2010 | Michelson |
| 7,799,081 | B2 | 9/2010 | McKinley |
| 7,799,083 | B2 | 9/2010 | Smith et al. |
| 7,819,921 | B2 | 10/2010 | Grotz |
| 7,824,445 | B2 | 11/2010 | Biro et al. |
| 7,837,734 | B2 | 11/2010 | Zucherman et al. |
| 7,846,206 | B2 | 12/2010 | Oglaza et al. |
| 7,850,733 | B2 | 12/2010 | Baynham et al. |
| 7,854,766 | B2 | 12/2010 | Moskowitz et al. |
| 7,874,980 | B2 | 1/2011 | Sonnenschein et al. |
| 7,879,098 | B1 | 2/2011 | Simmons |
| 7,887,589 | B2 | 2/2011 | Glenn et al. |
| 7,909,870 | B2 | 3/2011 | Kraus |
| 7,918,874 | B2 | 4/2011 | Siegal |
| 7,922,729 | B2 | 4/2011 | Michelson |
| 7,935,051 | B2 | 5/2011 | Miles et al. |
| 7,942,903 | B2 | 5/2011 | Moskowitz et al. |
| 7,947,078 | B2 | 5/2011 | Siegal |
| 7,951,199 | B2 | 5/2011 | Miller |
| 7,985,231 | B2 | 7/2011 | Sankaran |
| 7,993,403 | B2 | 8/2011 | Foley et al. |
| 8,007,535 | B2 | 8/2011 | Hudgins et al. |
| 8,021,424 | B2 | 9/2011 | Beger et al. |
| 8,021,426 | B2 | 9/2011 | Segal et al. |
| 8,025,697 | B2 | 9/2011 | McClellan et al. |
| 8,034,109 | B2 | 10/2011 | Zwirkoski |
| 8,043,381 | B2 | 10/2011 | Hestad et al. |
| 8,057,544 | B2 | 11/2011 | Schaller |
| 8,062,375 | B2 | 11/2011 | Glerum et al. |
| 8,075,621 | B2 | 12/2011 | Michelson |
| 8,177,812 | B2 | 5/2012 | Sankaran |
| 8,192,495 | B2 | 6/2012 | Simpson et al. |
| 8,206,423 | B2 | 6/2012 | Siegal |
| 8,221,501 | B2 | 7/2012 | Eiserman et al. |
| 8,221,502 | B2 | 7/2012 | Branch |
| 8,221,503 | B2 | 7/2012 | Garcia et al. |
| 8,231,681 | B2 | 7/2012 | Castleman et al. |
| 8,236,029 | B2 | 8/2012 | Siegal |
| 8,236,058 | B2 | 8/2012 | Fabian et al. |
| 8,241,328 | B2 | 8/2012 | Siegal |
| 8,241,358 | B2 | 8/2012 | Butler et al. |
| 8,246,622 | B2 | 8/2012 | Siegal et al. |
| 8,257,442 | B2 | 9/2012 | Edie et al. |
| 8,262,666 | B2 | 9/2012 | Baynham et al. |
| 8,267,939 | B2 | 9/2012 | Cipoletti et al. |
| 8,273,128 | B2 | 9/2012 | Oh et al. |
| 8,287,599 | B2 | 10/2012 | McGuckin |
| 8,303,663 | B2 | 11/2012 | Jimenez et al. |
| 8,323,345 | B2 | 12/2012 | Sledge |
| 8,328,812 | B2 | 12/2012 | Siegal et al. |
| 8,328,852 | B2 | 12/2012 | Zehavi et al. |
| 8,337,559 | B2 | 12/2012 | Hansell et al. |
| 8,343,193 | B2 | 1/2013 | Johnson et al. |
| 8,353,961 | B2 | 1/2013 | McClintock |
| 8,382,842 | B2 | 2/2013 | Greenhalgh et al. |
| 8,398,713 | B2 | 3/2013 | Weiman |
| 8,403,990 | B2 | 3/2013 | Dryer et al. |
| 8,409,291 | B2 | 4/2013 | Blackwell et al. |
| 8,435,298 | B2 | 5/2013 | Weiman |
| 8,454,617 | B2 | 6/2013 | Schaller et al. |
| 8,454,698 | B2 | 6/2013 | de Villiers et al. |
| 8,465,524 | B2 | 6/2013 | Siegal |
| 8,486,109 | B2 | 7/2013 | Siegal |
| 8,486,148 | B2 | 7/2013 | Butler et al. |
| 8,491,659 | B2 | 7/2013 | Weiman |
| 8,506,635 | B2 | 8/2013 | Palmatier et al. |
| 8,518,087 | B2 | 8/2013 | Morgenstern et al. |
| 8,518,120 | B2 | 8/2013 | Glerum et al. |
| 8,551,173 | B2 | 10/2013 | Lechmann et al. |
| 8,556,979 | B2 | 10/2013 | Glerum et al. |
| 8,568,481 | B2 | 10/2013 | Olmos et al. |
| 8,579,977 | B2 | 11/2013 | Fabian |
| 8,579,981 | B2 | 11/2013 | Lim et al. |
| 8,591,585 | B2 | 11/2013 | McLaughlin et al. |
| 8,597,330 | B2 | 12/2013 | Siegal |
| 8,628,576 | B2 | 1/2014 | Triplett et al. |
| 8,628,578 | B2 | 1/2014 | Miller et al. |
| 8,632,595 | B2 | 1/2014 | Weiman |
| 8,663,329 | B2 | 3/2014 | Ernst |
| 8,668,740 | B2 | 3/2014 | Rhoda et al. |
| 8,672,977 | B2 | 3/2014 | Siegal et al. |
| 8,679,183 | B2 | 3/2014 | Glerum et al. |
| 8,685,098 | B2 | 4/2014 | Glerum et al. |
| 8,696,751 | B2 | 4/2014 | Ashley et al. |
| 8,709,086 | B2 | 4/2014 | Glerum et al. |
| 8,715,351 | B1 | 5/2014 | Pinto |
| 8,721,723 | B2 | 5/2014 | Hansell et al. |
| 8,753,398 | B2 | 6/2014 | Gordon et al. |
| 8,771,360 | B2 | 7/2014 | Jimenez et al. |
| 8,777,993 | B2 | 7/2014 | Siegal et al. |
| 8,778,025 | B2 | 7/2014 | Ragab et al. |
| 8,795,366 | B2 | 8/2014 | Varela |
| 8,828,085 | B1 | 9/2014 | Jensen |
| 8,845,638 | B2 | 9/2014 | Siegal et al. |
| 8,845,731 | B2 | 9/2014 | Weiman |
| 8,845,732 | B2 | 9/2014 | Weiman |
| 8,845,734 | B2 | 9/2014 | Weiman |
| 8,852,279 | B2 | 10/2014 | Weiman |
| 8,864,833 | B2 | 10/2014 | Glerum et al. |
| 8,888,853 | B2 | 11/2014 | Glerum et al. |
| 8,888,854 | B2 | 11/2014 | Glerum et al. |
| 8,900,235 | B2 | 12/2014 | Siegal |
| 8,900,307 | B2 | 12/2014 | Hawkins et al. |
| 8,906,098 | B2 | 12/2014 | Siegal |
| 8,926,704 | B2 | 1/2015 | Glerum et al. |
| 8,936,641 | B2 | 1/2015 | Cain |
| 8,940,052 | B2 | 1/2015 | Lechmann et al. |
| 8,986,388 | B2 | 3/2015 | Siegal et al. |
| 9,017,408 | B2 | 4/2015 | Siegal et al. |
| 9,017,413 | B2 | 4/2015 | Siegal et al. |
| 9,044,334 | B2 | 6/2015 | Siegal et al. |
| 9,095,446 | B2 | 8/2015 | Landry et al. |
| 9,095,447 | B2 | 8/2015 | Barreiro et al. |
| 9,254,138 | B2 | 2/2016 | Siegal et al. |
| 9,283,092 | B2 | 3/2016 | Siegal et al. |
| 9,333,091 | B2 | 5/2016 | DiMauro |
| 9,408,712 | B2 | 8/2016 | Siegal et al. |
| 9,439,776 | B2 | 9/2016 | DiMauro et al. |
| 9,439,777 | B2 | 9/2016 | DiMauro |
| 2001/0039452 | A1 | 11/2001 | Zucherman et al. |
| 2001/0039453 | A1 | 11/2001 | Gresser et al. |
| 2001/0056302 | A1 | 12/2001 | Boyer et al. |
| 2002/0010070 | A1 | 1/2002 | Cales et al. |
| 2002/0029084 | A1 | 3/2002 | Paul et al. |
| 2002/0035400 | A1 | 3/2002 | Bryan et al. |
| 2002/0037799 | A1* | 3/2002 | Li .................. A61L 27/12 501/82 |
| 2002/0045904 | A1 | 4/2002 | Fuss et al. |
| 2002/0055781 | A1 | 5/2002 | Sazy |
| 2002/0058947 | A1 | 5/2002 | Hochschuler et al. |
| 2002/0068976 | A1 | 6/2002 | Jackson |
| 2002/0068977 | A1 | 6/2002 | Jackson |
| 2002/0077701 | A1 | 6/2002 | Kuslich |
| 2002/0107573 | A1 | 8/2002 | Steinberg |

(56) References Cited

U.S. PATENT DOCUMENTS

| | | |
|---|---|---|
| 2002/0128715 A1 | 9/2002 | Bryan et al. |
| 2002/0128716 A1 | 9/2002 | Cohen et al. |
| 2002/0151976 A1 | 10/2002 | Foley et al. |
| 2002/0165612 A1 | 11/2002 | Gerber et al. |
| 2002/0173796 A1 | 11/2002 | Cragg |
| 2002/0193883 A1 | 12/2002 | Wironen |
| 2002/0198526 A1 | 12/2002 | Shaolian et al. |
| 2003/0004575 A1 | 1/2003 | Erickson |
| 2003/0004576 A1 | 1/2003 | Thalgott |
| 2003/0006942 A1 | 1/2003 | Searls et al. |
| 2003/0014112 A1 | 1/2003 | Ralph et al. |
| 2003/0014116 A1 | 1/2003 | Ralph et al. |
| 2003/0023305 A1 | 1/2003 | McKay |
| 2003/0028251 A1 | 2/2003 | Mathews |
| 2003/0040799 A1 | 2/2003 | Boyd et al. |
| 2003/0045939 A1 | 3/2003 | Casutt |
| 2003/0065396 A1 | 4/2003 | Michelson |
| 2003/0069642 A1 | 4/2003 | Ralph et al. |
| 2003/0078667 A1 | 4/2003 | Manasas et al. |
| 2003/0130739 A1 | 7/2003 | Gerbec et al. |
| 2003/0135275 A1 | 7/2003 | Garcia et al. |
| 2003/0139812 A1 | 7/2003 | Garcia et al. |
| 2003/0139813 A1 | 7/2003 | Messerli et al. |
| 2003/0199979 A1 | 10/2003 | McGuckin |
| 2003/0204261 A1* | 10/2003 | Eisermann ............ A61F 2/4425 623/17.14 |
| 2003/0233145 A1 | 12/2003 | Landry et al. |
| 2004/0002761 A1 | 1/2004 | Rogers et al. |
| 2004/0010318 A1 | 1/2004 | Ferree |
| 2004/0030387 A1 | 2/2004 | Landry et al. |
| 2004/0049270 A1 | 3/2004 | Gewirtz |
| 2004/0064144 A1 | 4/2004 | Johnson et al. |
| 2004/0073310 A1 | 4/2004 | Moumene et al. |
| 2004/0087947 A1 | 5/2004 | Lim et al. |
| 2004/0088055 A1 | 5/2004 | Hanson et al. |
| 2004/0116997 A1 | 6/2004 | Taylor et al. |
| 2004/0117022 A1 | 6/2004 | Marnay et al. |
| 2004/0127990 A1 | 7/2004 | Bartish, Jr. et al. |
| 2004/0127991 A1 | 7/2004 | Ferree |
| 2004/0143332 A1 | 7/2004 | Krueger et al. |
| 2004/0153065 A1 | 8/2004 | Lim |
| 2004/0153156 A1 | 8/2004 | Cohen et al. |
| 2004/0162618 A1 | 8/2004 | Mujwid et al. |
| 2004/0172133 A1 | 9/2004 | Gerber et al. |
| 2004/0186570 A1 | 9/2004 | Rapp |
| 2004/0186577 A1 | 9/2004 | Ferree |
| 2004/0193277 A1 | 9/2004 | Long |
| 2004/0220669 A1 | 11/2004 | Studer |
| 2004/0230309 A1 | 11/2004 | DiMauro |
| 2004/0267367 A1 | 12/2004 | O'Neil |
| 2005/0019365 A1 | 1/2005 | Frauchiger et al. |
| 2005/0038515 A1 | 2/2005 | Kunzler |
| 2005/0113916 A1 | 5/2005 | Branch |
| 2005/0113917 A1 | 5/2005 | Chae et al. |
| 2005/0119752 A1 | 6/2005 | Williams et al. |
| 2005/0125062 A1 | 6/2005 | Biedermann et al. |
| 2005/0165485 A1 | 7/2005 | Trieu |
| 2005/0197702 A1 | 9/2005 | Coppes et al. |
| 2005/0222681 A1 | 10/2005 | Richley et al. |
| 2005/0256576 A1 | 11/2005 | Moskowitz et al. |
| 2005/0261682 A1 | 11/2005 | Ferree |
| 2005/0261769 A1 | 11/2005 | Moskowitz et al. |
| 2005/0278026 A1 | 12/2005 | Gordon et al. |
| 2006/0036241 A1 | 2/2006 | Siegal |
| 2006/0058876 A1 | 3/2006 | McKinley |
| 2006/0058880 A1 | 3/2006 | Wysocki |
| 2006/0100706 A1 | 5/2006 | Shadduck et al. |
| 2006/0111785 A1 | 5/2006 | O'Neil |
| 2006/0122701 A1 | 6/2006 | Kiester |
| 2006/0122703 A1 | 6/2006 | Aebi et al. |
| 2006/0129244 A1 | 6/2006 | Ensign |
| 2006/0136062 A1 | 6/2006 | DiNello et al. |
| 2006/0142858 A1 | 6/2006 | Colleran et al. |
| 2006/0206207 A1 | 9/2006 | Dryer et al. |
| 2006/0235531 A1 | 10/2006 | Buettner |
| 2006/0253201 A1 | 11/2006 | McLuen |
| 2006/0265075 A1 | 11/2006 | Baumgartner et al. |
| 2006/0265077 A1 | 11/2006 | Zwirkoski |
| 2007/0010886 A1 | 1/2007 | Banick et al. |
| 2007/0055377 A1 | 3/2007 | Hanson et al. |
| 2007/0118222 A1 | 5/2007 | Lang |
| 2007/0149978 A1 | 6/2007 | Shezifi et al. |
| 2007/0173939 A1 | 7/2007 | Kim et al. |
| 2007/0173940 A1 | 7/2007 | Hestad et al. |
| 2007/0178222 A1 | 8/2007 | Storey et al. |
| 2007/0191959 A1 | 8/2007 | Hartmann et al. |
| 2007/0198089 A1 | 8/2007 | Moskowitz et al. |
| 2007/0208423 A1 | 9/2007 | Messerli et al. |
| 2007/0219634 A1 | 9/2007 | Greenhalgh et al. |
| 2007/0233244 A1 | 10/2007 | Lopez et al. |
| 2007/0270968 A1 | 11/2007 | Baynham et al. |
| 2007/0276375 A1 | 11/2007 | Rapp |
| 2007/0299521 A1 | 12/2007 | Glenn |
| 2008/0009877 A1 | 1/2008 | Sankaran et al. |
| 2008/0015701 A1 | 1/2008 | Garcia et al. |
| 2008/0021556 A1 | 1/2008 | Edie |
| 2008/0021558 A1 | 1/2008 | Thramann |
| 2008/0027550 A1 | 1/2008 | Link et al. |
| 2008/0033440 A1 | 2/2008 | Moskowitz et al. |
| 2008/0058944 A1 | 3/2008 | Duplessis et al. |
| 2008/0065219 A1 | 3/2008 | Dye |
| 2008/0082173 A1 | 4/2008 | Delurio et al. |
| 2008/0132934 A1 | 6/2008 | Reilly |
| 2008/0140207 A1 | 6/2008 | Olmos |
| 2008/0147193 A1 | 6/2008 | Matthis et al. |
| 2008/0161927 A1 | 7/2008 | Savage et al. |
| 2008/0167657 A1 | 7/2008 | Greenhalgh |
| 2008/0177388 A1 | 7/2008 | Patterson et al. |
| 2008/0183204 A1 | 7/2008 | Greenhalgh et al. |
| 2008/0188945 A1 | 8/2008 | Boyce et al. |
| 2008/0195209 A1 | 8/2008 | Garcia et al. |
| 2008/0243251 A1 | 10/2008 | Stad et al. |
| 2008/0243254 A1 | 10/2008 | Butler |
| 2008/0249622 A1 | 10/2008 | Gray |
| 2008/0281425 A1 | 11/2008 | Thalgott |
| 2009/0005873 A1 | 1/2009 | Slivka et al. |
| 2009/0030423 A1 | 1/2009 | Puno |
| 2009/0054991 A1 | 2/2009 | Biyani |
| 2009/0076610 A1 | 3/2009 | Afzal |
| 2009/0099568 A1 | 4/2009 | Lowry et al. |
| 2009/0112320 A1 | 4/2009 | Kraus |
| 2009/0112324 A1 | 4/2009 | Refai et al. |
| 2009/0164020 A1 | 6/2009 | Janowski |
| 2009/0177281 A1 | 7/2009 | Swanson et al. |
| 2009/0177284 A1 | 7/2009 | Rogers et al. |
| 2009/0222096 A1 | 9/2009 | Trieu |
| 2009/0222099 A1 | 9/2009 | Liu et al. |
| 2009/0234398 A1 | 9/2009 | Chirico et al. |
| 2009/0240335 A1 | 9/2009 | Arcenio et al. |
| 2009/0248159 A1 | 10/2009 | Aflatoon |
| 2009/0292361 A1 | 11/2009 | Lopez et al. |
| 2010/0016905 A1 | 1/2010 | Greenhalgh et al. |
| 2010/0076559 A1 | 3/2010 | Bagga |
| 2010/0179594 A1 | 7/2010 | Theofilos et al. |
| 2010/0234956 A1 | 9/2010 | Attia et al. |
| 2010/0262240 A1 | 10/2010 | Chavatte et al. |
| 2010/0286783 A1 | 11/2010 | Lechmann et al. |
| 2010/0324607 A1 | 12/2010 | Davis |
| 2011/0004308 A1 | 1/2011 | Marino et al. |
| 2011/0004310 A1 | 1/2011 | Michelson |
| 2011/0015747 A1 | 1/2011 | McManus et al. |
| 2011/0029082 A1 | 2/2011 | Hall |
| 2011/0035011 A1 | 2/2011 | Cain |
| 2011/0093074 A1 | 4/2011 | Glerum et al. |
| 2011/0098818 A1 | 4/2011 | Brodke et al. |
| 2011/0130835 A1 | 6/2011 | Ashley et al. |
| 2011/0130838 A1 | 6/2011 | Morgenstern et al. |
| 2011/0144753 A1 | 6/2011 | Marchek et al. |
| 2011/0172716 A1 | 7/2011 | Glerum |
| 2011/0270261 A1 | 11/2011 | Mast et al. |
| 2011/0282453 A1 | 11/2011 | Greenhalgh et al. |
| 2011/0301711 A1 | 12/2011 | Palmatier et al. |
| 2011/0301712 A1 | 12/2011 | Palmatier et al. |
| 2012/0004726 A1 | 1/2012 | Greenhalgh et al. |

(56) References Cited

U.S. PATENT DOCUMENTS

| | | |
|---|---|---|
| 2012/0004732 A1 | 1/2012 | Goel et al. |
| 2012/0022654 A1 | 1/2012 | Farris et al. |
| 2012/0029636 A1 | 2/2012 | Ragab et al. |
| 2012/0071977 A1 | 3/2012 | Oglaza et al. |
| 2012/0071980 A1 | 3/2012 | Purcell et al. |
| 2012/0083889 A1 | 4/2012 | Purcell et al. |
| 2012/0123546 A1 | 5/2012 | Medina |
| 2012/0197403 A1 | 8/2012 | Merves |
| 2012/0226357 A1 | 9/2012 | Varela |
| 2012/0290097 A1 | 11/2012 | Cipoletti et al. |
| 2012/0310350 A1 | 12/2012 | Farris et al. |
| 2012/0310352 A1 | 12/2012 | DiMauro et al. |
| 2013/0030536 A1 | 1/2013 | Rhoda et al. |
| 2013/0085572 A1 | 4/2013 | Glerum et al. |
| 2013/0085574 A1 | 4/2013 | Sledge |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190875 A1 | 7/2013 | Shulock et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0310939 A1 | 11/2013 | Fabian et al. |
| 2014/0039622 A1 | 2/2014 | Glerum et al. |
| 2014/0046333 A1 | 2/2014 | Johnson et al. |
| 2014/0058513 A1 | 2/2014 | Gahman et al. |
| 2014/0067073 A1 | 3/2014 | Hauck |
| 2014/0114423 A1 | 4/2014 | Suedkamp et al. |
| 2014/0128977 A1 | 5/2014 | Glerum et al. |
| 2014/0135934 A1 | 5/2014 | Hansell et al. |
| 2014/0142706 A1 | 5/2014 | Hansell et al. |
| 2014/0163683 A1 | 6/2014 | Seifert et al. |
| 2014/0172106 A1 | 6/2014 | To et al. |
| 2014/0180421 A1 | 6/2014 | Glerum et al. |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0303731 A1 | 10/2014 | Glerum et al. |
| 2014/0303732 A1 | 10/2014 | Rhoda et al. |
| 2014/0324171 A1 | 10/2014 | Glerum et al. |
| 2015/0094812 A1 | 4/2015 | Cain |
| 2015/0112437 A1 | 4/2015 | Davis et al. |
| 2015/0164655 A1 | 6/2015 | DiMauro |
| 2015/0173914 A1 | 6/2015 | DiMauro et al. |
| 2015/0196401 A1 | 7/2015 | DiMauro et al. |
| 2015/0202052 A1 | 7/2015 | DiMauro |
| 2015/0216673 A1 | 8/2015 | DiMauro |
| 2016/0000577 A1 | 1/2016 | DiMauro |
| 2016/0022437 A1 | 1/2016 | Kelly et al. |
| 2016/0038304 A1 | 2/2016 | Aquino Shluzas et al. |
| 2016/0051376 A1 | 2/2016 | Serhan et al. |
| 2016/0058573 A1 | 3/2016 | DiMauro et al. |
| 2016/0074175 A1 | 3/2016 | O'Neil |
| 2016/0199196 A1 | 7/2016 | Serhan et al. |
| 2016/0310296 A1 | 10/2016 | DiMauro et al. |
| 2016/0317313 A1 | 11/2016 | DiMauro |
| 2016/0317714 A1 | 11/2016 | DiMauro et al. |

FOREIGN PATENT DOCUMENTS

| | | |
|---|---|---|
| DE | 3911610 | 10/1990 |
| DE | 4012622 | 7/1997 |
| DE | 202008001079 | 3/2008 |
| EP | 282161 | 9/1988 |
| EP | 678489 | 10/1995 |
| EP | 1290985 | 3/2003 |
| EP | 1532949 | 5/2005 |
| EP | 1541096 | 6/2005 |
| EP | 1385449 B1 | 7/2006 |
| EP | 1683593 | 7/2006 |
| EP | 1698305 B1 | 8/2007 |
| EP | 1843723 B1 | 3/2010 |
| EP | 2368529 | 9/2011 |
| EP | 2237748 B1 | 9/2012 |
| EP | 2764851 | 8/2014 |
| FR | 2718635 | 10/1995 |
| FR | 2730159 | 8/1996 |
| FR | 2874814 | 3/2006 |
| JP | 2003-526457 | 9/2003 |
| JP | 2006-516456 | 7/2006 |
| JP | 2011-509766 A | 3/2011 |
| WO | WO 93/17669 | 9/1993 |
| WO | WO 1994/004100 | 3/1994 |
| WO | WO 1995/031158 | 11/1995 |
| WO | WO 97/00054 | 1/1997 |
| WO | WO 97/26847 | 7/1997 |
| WO | WO 99/02214 | 1/1999 |
| WO | WO 1999/053871 | 10/1999 |
| WO | WO 00/12033 | 3/2000 |
| WO | WO 00/13620 | 3/2000 |
| WO | WO 2000/053127 | 9/2000 |
| WO | WO 00/74605 | 12/2000 |
| WO | WO 01/01895 | 1/2001 |
| WO | WO 2001/001893 | 1/2001 |
| WO | WO 2001/017464 | 3/2001 |
| WO | WO 02/17825 | 3/2002 |
| WO | WO 03/002021 | 1/2003 |
| WO | WO 03/005937 | 1/2003 |
| WO | WO 2005/112834 | 12/2005 |
| WO | WO 2006/047587 | 5/2006 |
| WO | WO 2006/058281 | 6/2006 |
| WO | WO 2006/065419 | 6/2006 |
| WO | WO 2006/081843 | 8/2006 |
| WO | WO 2007/028098 | 3/2007 |
| WO | WO 2007/048012 | 4/2007 |
| WO | WO 2008/044057 | 4/2008 |
| WO | WO 2007/009107 | 8/2008 |
| WO | WO 2009/092102 | 7/2009 |
| WO | WO 2009/064787 | 8/2009 |
| WO | WO 2009/124269 | 10/2009 |
| WO | WO 2009/143496 | 11/2009 |
| WO | WO 2010/068725 | 6/2010 |
| WO | WO 2010/148112 | 12/2010 |
| WO | WO 2011/142761 | 11/2011 |
| WO | WO 2012/009152 | 1/2012 |
| WO | WO 2012/089317 | 7/2012 |
| WO | WO 2012/135764 | 10/2012 |
| WO | WO 2013/006669 | 1/2013 |
| WO | WO 2013/023096 | 2/2013 |
| WO | WO 2013/025876 | 2/2013 |
| WO | WO 2013/043850 | 5/2013 |
| WO | WO 2013/082184 | 6/2013 |
| WO | WO 2013/158294 | 10/2013 |
| WO | WO 2013/173767 | 11/2013 |
| WO | WO 2013/184946 | 12/2013 |
| WO | WO 2014/018098 | 1/2014 |
| WO | WO 2014/026007 | 2/2014 |
| WO | WO 2014/035962 | 3/2014 |
| WO | WO 2014/088521 | 6/2014 |
| WO | WO 2014/116891 | 7/2014 |

OTHER PUBLICATIONS

Ha et al. (Topographical characterization and microstructural interface analysis of vacuum-plasma-sprayed titanium and hydroxyapatite coatings on carbon fiber-reinforced poly(etheretherketone), Journal of Materials Science: Materials in Science 9 (1997), pp. 891-896.*

Nguyen et al., Poly(Aryl-Ether-Ether-Ketone) and its Advanced Composites: A Review, Polymer Composites, Apr. 1987, vol. 8, No. 2.*

U.S. Appl. No. 61/675,975, filed Jul. 26, 2012, Lechmann et al.

(56) References Cited

OTHER PUBLICATIONS

Hoogland, T. et al., Total Lumbar Intervertebral Disc Replacement: testing of a New Articulating Space in Human Cadaver Spines—24 1 Annual ORS, Dallas TX, Feb. 21-23, 1978, 8 pages.
European Search Report EP03253921 dated Nov. 13, 2003, 4 pages.
Link SB Charite Brochure—Intervertebral Prosthesis 1988, 29 pages.
Spine Solutions Brochure—Prodisc 2001, 16 pages.
Chiang, Biomechanical Comparison of Instrumented Posterior Lumbar Interbody Fusion with One or Two Cages by Finite Element Analysis, Spine, 2006, pp. E682-E689, vol. 31(19), Lippincott Williams & Wilkins, Inc.
Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Gore, Technique of Cervical Interbody Fusion, Clinical Orthopaedics and Related Research, 1984, pp. 191-195, No. 188.
Hunt, Expanable cage placement via a posterolateral approach in lumbar spine reconstructions, Journal of Neurosurgery: Spine, 2006, pp. 271-274, vol. 5.
Krbec, [Replacement of the vertebral body with an expansion implant (Synex)], Acta Chir Orthop Traumatol Cech, 2002, pp. 158-162, vol. 69(3).
Polikeit, The importance of the endplate for interbody cages in the lumbar spine, Eur Spine J, 2003, pp. 556-561, vol. 12.
Shin, Posterior Lumbar Interbody Fusion via a Unilateral Approach, Yonsei Medical Journal, 2006, pp. 319-325, vol. 47(3).
https://emea.depuysynthes.com/hcp/hip/products/qs/porocoat-porous-coating-emea, Porocoat® Porous Coating, Depuy Synthes, webpage, accessed Jul. 5, 2016.
Cheng, B.C., Ph.D., Biomechanical pullout strength and histology of Plasmapore® XP coated implants: Ovine multi time point survival study. Aesculap Implant Systems, LLC, 2013, 12 pages.
Kotsias, A., Clinical trial of titanium-coated PEEL cages anterior cervical discectomy and fusion. [Klinishe Untersuching zum Einsatz von titanbeschichteten Polyetheretherketon-Implantaten bei der cervikalen interkorporalen fusion]. Doctoral thesis. Department of Medicine, Charite, University of Medicine Berlin, 2014, 73 pages. (German language document/Engl. summary).
Cambridge Scientific News, FDA Approves Cambridge Scientific, Inc.'s Orthopedic WISORB (TM) Malleolar Screw [online], Jul. 30, 2002 [retrieved on Oct. 14 2003]. Retrieved from the Internet <URL: http://www.cambridgescientificinc.com>.
Zimmer.com, Longer BAK/L Sterile Interbody Fusion Devices. Date believed to be 1997. Product Data Sheet.Zimmer. Retrieved Jul. 23, 2012 from <http://catalog.zimmer.com/content/zpc/products/600/600/620/S20/S045.html>, 2 pages.
OSTEOSET® DBM Pellets (Important Medical Information) [online], Nov. 2002 [retrieved on Oct. 14, 2003]. Retrieved from the Internet <URL: http://www.wmt.com/Literature>.
Sonic Accelerated Fracture Healing System/Exogen 3000. Premarket Approval. U.S. Food & Drug Administration. Date believed to be May 10, 2000. Retrieved Jul. 23, 2012 from <http://www.accessdata.fda.gov/scripts/cdrh/cfdocs/cfPMA/pma.cfm?id=14736#>. 4 pages, 2012.
Bruder et al., Identification and characterization of a cell surface differentiation antigen on human osteoprogenitor cells. 42nd Annual Meeting of the Orthopaedic Research Society. p. 574, Feb. 19-22, 1996, Atlanta, Georgia.
Bruder et al., Monoclonal antibodies reactive with human osteogenic cell surface antigens. Bone. Sep. 1997;21 (3):225-235.
Burkoth et al., A review of photocrosslinked polyanhydrides: in situ forming degradable networks. Biomaterials. Dec. 2000;21 (23 ):2395-2404.
Flemming et al., Monoclonal anitbody against adult marrow-derived mesenchymal stem cells recognizes developing vasculature in embryonic human skin. Developmental Dynamics. 1998;212:119-132.
Haas, Norbert P., New Products from AO Development [online], May 2002 [retrieved on Oct. 14, 2003]. Retrieved from the Internet <URL: http://www.ao.asif.ch/development/pdf_tk_news_02.pdf>.
Hao et al., Investigation of nanocomposites based on semi-interpenetrating network of [L-poly (epsilon-caprolactone )]/[net-poly ( epsilon-caprolactone )] and hydroxyapatite nanocrystals. Biomaterials. Apr. 2003;24(9): 1531-9.
Haynesworth et al., Cell surface antigens on human marrow-derived mesenchymal cells are detected by monoclonal antibodies. Bone. 1992;13(1):69-80.
Hitchon et al., Comparison of the biomechanics of hydroxyapatite and polymethylmethacrylate vertebroplasty in a cadaveric spinal compression fracture model. J Neurosurg. Oct. 2001;95(2 Suppl):215-20.
Kandziora, Frank, et al., "Biomechanical Analysis of Biodegradable Interbody Fusion Cages Augmented with Poly (propylene Glycol-co-Fumaric Acid)," Spine, 27(15): 1644-1651 (2002).
Kroschwitz et al., eds., Hydrogels. Concise Encyclopedia of Polymer Science and Engineering. Wiley and Sons, pp. 458-459, 1990.
Lendlein et al., AB-polymer networks based on oligo(epsilon-caprolactone) segments showing shape-memory properties. Proc Natl Acad Sci US A. Jan. 30, 2001;98(3):842-7. Epub Jan. 23, 2001.
Malberg. M.I., MD; Pimenta, L., MD; Millan, M.M., MD, 9th International Meeting on Advanced Spine Techniques, May 23-25, 2002, Montreux, Switzerland. Paper #54, Paper #60, and E-Poster #54, 5 pages.
McAfee et al., Minimally invasive anterior retroperitoneal approach to the lumbar spine: Emphasis on the lateral BAK. SPINE. 1998;23(13):1476-84.
Mendez et al., Self-curing acrylic formulations containing PMMA/ PCL composites: properties and antibiotic release behavior. J Biomed Mater Res. Jul. 2002;61 (1 ):66-74.
Regan et al., Endoscopic thoracic fusion cage. Atlas of Endoscopic Spine Surgery. Quality Medical Publishing, Inc. 1995;350-354.
Slivka et al., In vitro compression testing of fiber-reinforced, bioabsorbable, porous implants. Synthetic Bioabsorbable Polymers for Implants. STP1396, pp. 124-135, ATSM International, Jul. 2000.
Stewart et al., Co-expression of the stro-1 anitgen and alkaline phosphatase in cultures of human bone and marrow cells. ASBMR 18th Annual Meeting. Bath Institute for Rheumatic Diseases, Bath, Avon, UK. Abstract No. P208, p. S142, 1996.
Timmer et al., In vitro degradation of polymeric networks of poly(propylene fumarate) and the crosslinking macromer poly(propylene fumarate )-diacrylate. Biomaterials. Feb. 2003;24(4 ):571-7.
United States Disctrict Court, Central District of California, Case No. 1 :10-CV-00849-LPS, *Nuvasive, Inc.,* vs., *Globus Medical, Inc.*, Videotaped Deposition of: Luiz Pimenta, M.D., May 9, 2012, 20 pages.
Walsh et al., Preparation of porous composite implant materials by in situ polymerization of porous apatite containing epsilon-caprolactone or methyl methacrylate. Biomaterials. Jun. 2001;22( 11):1205-12.

\* cited by examiner

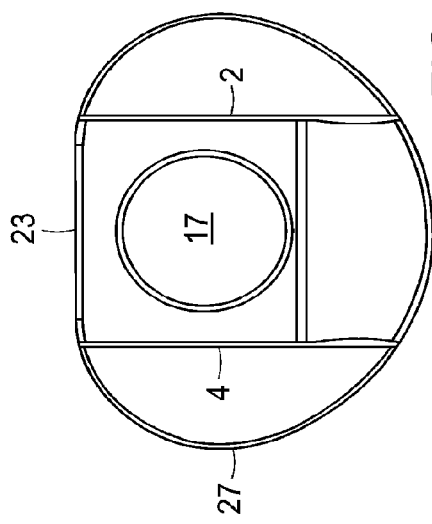
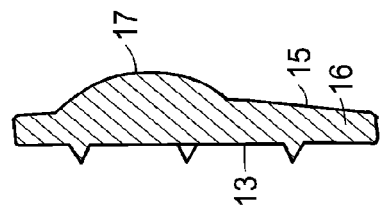
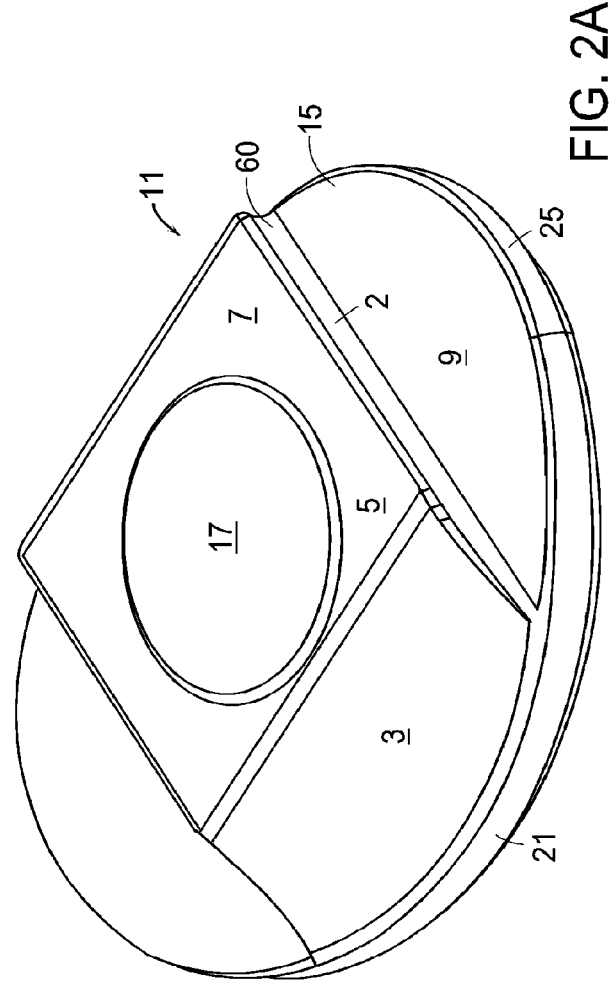
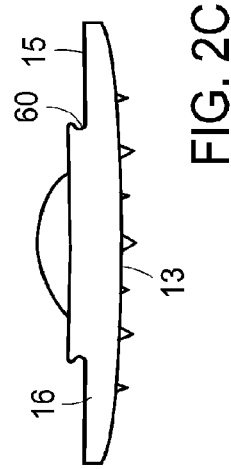

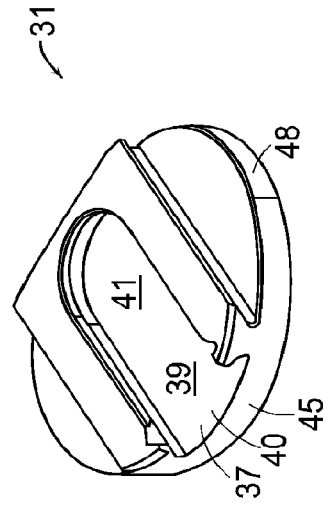
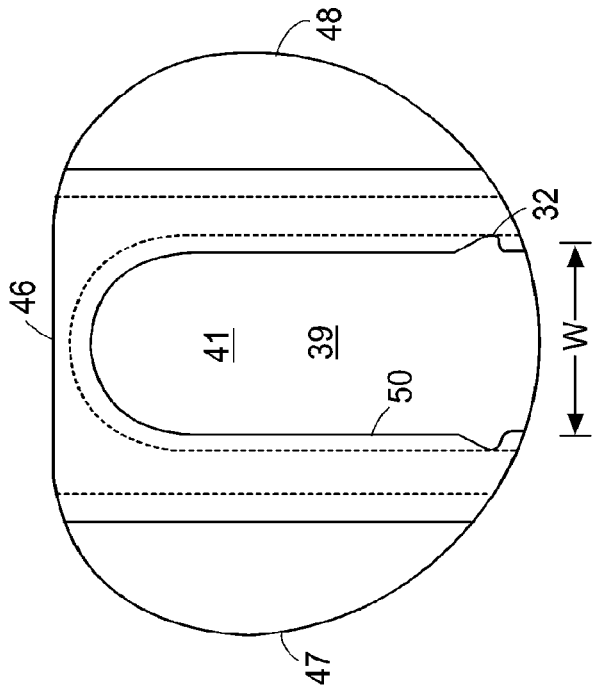
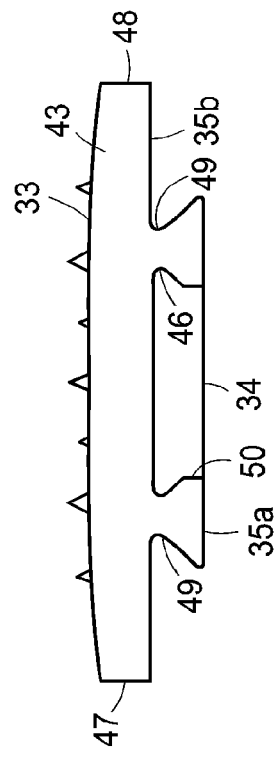

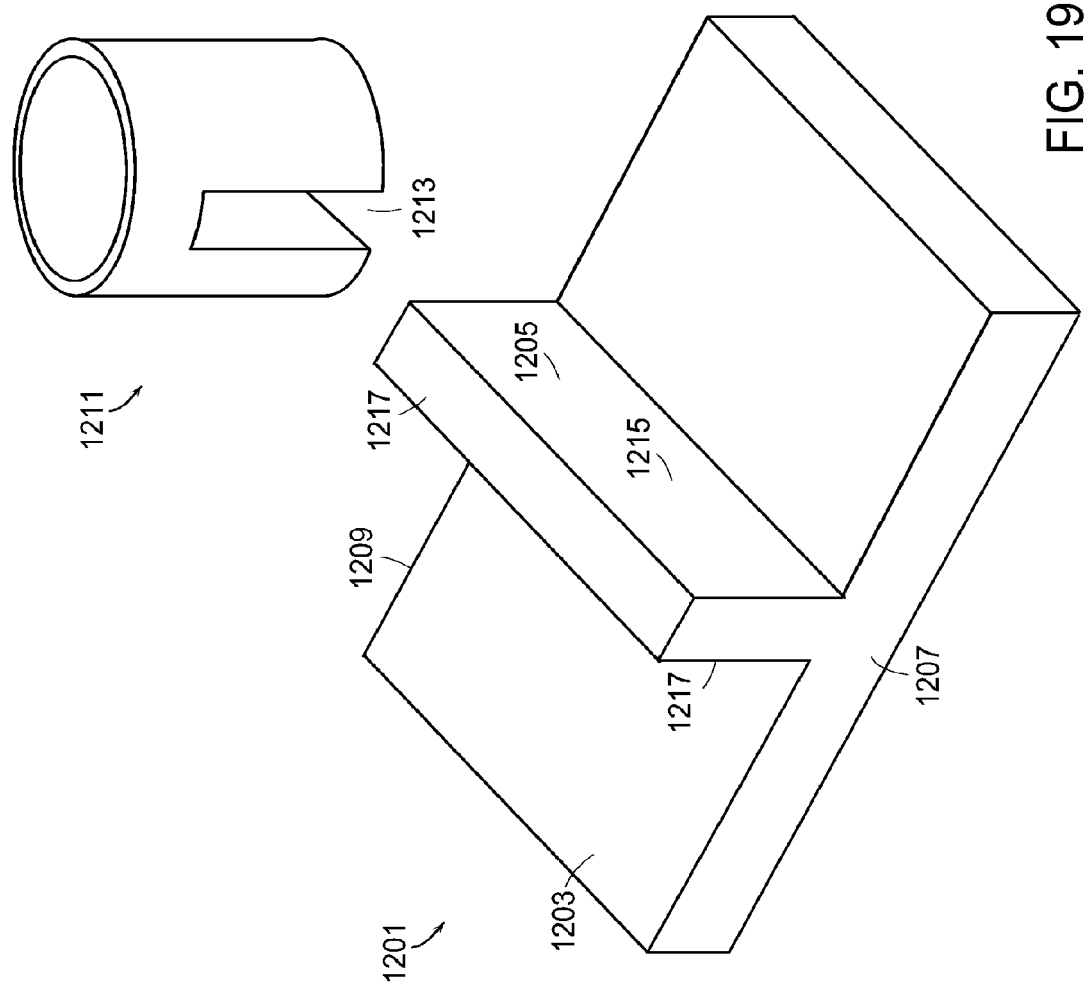

10,238,500 B2

INTERVERTEBRAL DISC

CROSS-REFERENCE TO RELATED APPLICATIONS

This is a divisional application of U.S. patent application Ser. No. 12/395,606 filed Feb. 27, 2009, which in turn is a divisional application of U.S. patent application Ser. No. 10/465,277 filed Jun. 19, 2003, which in turn claims priority to U.S. Provisional Patent Application Ser. No. 60/391,845 filed Jun. 27, 2002.

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of articulation weight through a damaged, unstable vertebral joint. One proposed method of managing these problems is to remove the problematic disc and replace it with a prosthetic disc that allows for the natural motion between the adjacent vertebrae ("a motion disc").

U.S. Pat. No. 6,368,350 ("Erickson") discloses a three-piece motion disc providing two articulation surfaces. The disc comprises a first piece having a curved surface, a second piece having a flat surface, and an intermediate piece having a corresponding curved articulation surface and a corresponding flat articulation surface. In many embodiments, the translation freedom of the intermediate piece is limited by a raised lip integrally formed around the edge of a flat surface upon the lower piece. Erickson teaches that the overall height of the device is varied by increasing or decreasing the thickness of one or more of the first, second or intermediate pieces. Erickson teaches that known methods for insertion of intervertebral prosthetic devices can be used for insertion of its device. Lastly, Erickson teaches that a variety of materials can be selected as materials of construction for the components of its device, including metals, polymers, and ceramics, and specifically teaches preferred combinations including metal-metal or metal-plastic combinations.

In each of Erickson's embodiments having a peripheral raised lip, the height of the core member appears to exceed the distance between the peripheral raised lips of the opposing endplates. Accordingly, the core member can not be inserted between the prosthetic endplates without overdistracting the disc space.

Erickson does not teach an open ended channel for inserting the intermediate piece between the prosthetic endplates, nor an additional component for retaining the intermediate piece upon the flat surface. Erickson does not teach piecemeal insertion of the device into the disc space. Erickson does not teach a metal-ceramic articulation interface.

U.S. Pat. No. 5,676,701 ("Yuan") discloses, in one embodiment, a motion disc having a single articulation surface. This device includes a first component whose inner surface comprises a concave inner portion having a 360° circumference and a convex peripheral portion, and an opposing second component whose inner surface comprises a conforming convex inner portion and a convex peripheral portion. The convex/concave contours of the opposing inner portions forms a ball-and-socket design that allows unrestricted pivotal motion of the device, while the opposing convex peripheral contours allow flexion/extension bending motion in the range of about 20-30°

In another embodiment, Yuan discloses a device having two articulation interfaces, wherein one of the above-mentioned components is made in two pieces having opposing flat surfaces that form a translation interface to further provide the prosthetic with a certain amount of translation. See FIG. 9 of Yuan. Yuan discloses that the translation-producing pieces can be fitted together mechanically, via shrink-fit, or by welding methods.

However, Yuan does not disclose an open-ended channel for fitting the translation producing pieces.

U.S. Pat. No. 5,507,816 ("Bullivant") discloses a three-piece motion disc providing two articulation interfaces and comprises an upper piece having a flat lower surface, a middle spacer having a flat upper surface and a convex lower surface, and a lower piece having a concave upper surface. The articulating convex and concave surfaces form an articulating interface that allows pivotal motion, while the flat surfaces form a translation interface that allows translational motion. Bullivant further teaches that the natural tension of the vertebrae ensures that the vertebrae are biased together to trap the spacer in place, and that the 90° extension of the convex and concave surfaces virtually eliminates any chance of the spacer escaping from between the plates under normal pivotal movement of the vertebrae.

The Bullivant device does not possess any channel for retaining the middle spacer within the device. Accordingly, it is prone to disengagement.

In each of the Erickson, Yuan, and Bullivant designs, the core member has a flat translation surface and a curved articulation surface.

There are currently two primary competitive artificial disc replacement devices on the market that are designed for the lumbar spine.

The first device has two articulation interfaces and comprises three components: an inferior endplate, a superior endplate, and a core. Both the inferior and superior endplates are metal and have raised bosses with concave spherical surfaces in the center. The core is plastic and has convex surfaces on both the top and bottom which are surrounded by raised rims.

However, this device does not have an open ended channel for inserting the core between the endplates. Related devices are disclosed in U.S. Pat. Nos. 4,759,766; 5,401,269; and 5,556,431.

In each of the devices disclosed in these three patents, the core member has either two concave surfaces or two convex surfaces.

The second device has a single articulation interface and comprises three components: an inferior endplate, a superior endplate, and a plastic insert. The inferior endplate functions as a baseplate and has a sidewall forming an open ended channel for reception of the insert. The inner surface of the inferior endplate provides only stationary support for the insert and does not have a motion surface. Since the plastic insert is designed to be locked securely into place within the inferior endplate, the inferior surface of the insert is not a motion surface. The superior surface of the insert includes articulation surface for articulation with the superior endplate. The superior endplate has an inferior articulation surface that articulates with the superior motion surface of the plastic insert, and a superior surface designed for attachment to a vertebral endplate. A related device is disclosed in U.S. Pat. No. 5,314,477.

The second device does not have two articulation surfaces. The second device relies upon downward-extending flexible tabs disposed upon the insert to keep the insert within the open-ended channel. These tabs eliminate any ability for the insert to translate with the adjacent endplate surfaces.

French Published Patent Application No. 2,730,159 ("Germain") discloses a motion disc in which the core member has one convex and concave surface. Germain further teaches that the radius of the upper curved surface (3a) of the core member is less than the radius of the lower curved surface (3b) of the core member.

Therefore, there is a need for a motion device having two articulation interfaces that allows for initial insertion of the prosthetic endplates into the disc space and then insertion therebetween of a core member having two articulation surfaces.

SUMMARY OF THE INVENTION

The present inventors have developed a motion disc having two articulation interfaces and an open ended channel. The two articulation interfaces allow the motion disc to more fully restore the natural motion of the spine than would a single articulation interface. The open ended channel allows for initial insertion of the prosthetic endplates into the disc space and then insertion therebetween of a core member having two articulation surfaces, thereby lessening the extent of required overdistraction.

Therefore, in accordance with the present invention, there is provided a prosthetic vertebral endplate comprising:
 i) an outer surface adapted to mate with a vertebral body,
 ii) an inner surface having a first opening thereon,
 iii) a body portion connecting the inner and outer surfaces and defining a sidewall comprising a second opening thereon, and
 iv) an articulation surface suitable for supporting articulation motion,
wherein the first and second openings communicate to form a channel having a first open end.

Also in accordance with the present invention, there is provided an intervertebral motion disc comprising: a) a prosthetic vertebral endplate comprising: [
 i) an outer surface adapted to mate with a vertebral body,
 ii) an inner surface having a first opening thereon,
 iii) a body portion connecting the inner and outer surfaces and defining a sidewall comprising a second opening thereon, and
 iv) a first articulation surface suitable for supporting articulation motion.
wherein the first and second openings communicate to form a channel having a first open end, and
b) a core member having a first articulation surface suitable for supporting articulation motion, wherein the core member is disposed within the channel and oriented therein to produce a first articulation interface between the first articulation surface of the first endplate and the first articulation surface of the core member.

The disc of the present invention is superior to that of Erickson, Yuan and the first commercial device in that the core member can be inserted through the open ended channel, thereby allowing for initial insertion of the prosthetic endplates into the disc space and then insertion therebetween of a core member having two articulation surfaces through the channel, and lessening the extent of required overdistraction.

The disc of the present invention is superior to that of Bullivant in that the channel helps retain the core member between the endplates and so need not rely upon natural ligament tension to retain the core member between the endplates, and prevents excessive lateral motion of the core.

The disc of the present invention is superior to that of the second commercial device in that its two articulation interfaces allow the motion disc to more fully restore the natural motion of the spine than would a single articulation interface.

DESCRIPTION OF THE FIGURES

FIGS. 2a, 2b, 2c, and 2d disclose isometric, cross-sectional, front and elevated views of the inferior endplate of the first embodiment of the present invention.

FIGS. 3a, 3b, and 3c disclose isometric, elevated and front views of the superior endplate of the first embodiment of the present invention.

FIG. 19 discloses a first endplate having a horizontally-extending projection and a core member having a recess for mating with the projection.

DETAILED DESCRIPTION OF THE INVENTION

For the purposes of the present invention, "prosthetic vertebral endplate" broadly describes a component designed to substantially fit within an interverterbal space and mate with an opposing surface of one of the adjacent vertebral bodies. The "prosthetic vertebral endplate" includes all geometric configurations, including but not limited to substantially thin and substantially blocky configurations. Types of mating include, but are not limited to, penetrating the adjacent vertebral body, simply contacting the adjacent vertebral body, and providing fixation through a third component such as a fastener (such as a screw) that is received within or connected to the prosthetic vertebral endplate. Such fixation may occur upon a non-opposing surface of the adjacent vertebral body (such as the anterior wall of the vertebral body). The adjacent vertebral body may be prepared or unprepared so that the contacting surface thereof may include the cortical end endplate portion of the vertebral body or the internal cancellous portion of the vertebral body.

For the purposes of the present invention, a "substantially curved articulation interface" produces substantially pivotal motion during articulation. Examples of such substantially curved interfaces include but are not limited to hemipsherical interfaces having a radius of between about 10 mm and about 30 mm.

For the purposes of the present invention, both "slightly curved articulation interfaces" and "substantially flat articulation interfaces" produce substantially translational motion during articulation. Examples of such "slightly curved interfaces" include but are not limited to hemispherical interfaces having a radius of between about 40 mm and about 100 mm. For the purposes of the present invention, a "substantially flat articulation interface" is sufficiently flat so as to allow axial rotation of either mating component at any point along the interface.

Figure 1A:
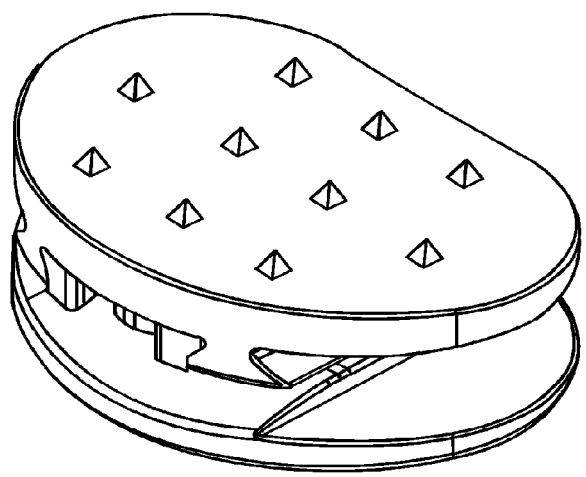
FIGS. 1a, 1b, and 1c disclose isometric, cross-sectional and front views of a first embodiment of the present invention.
Figure 1B:
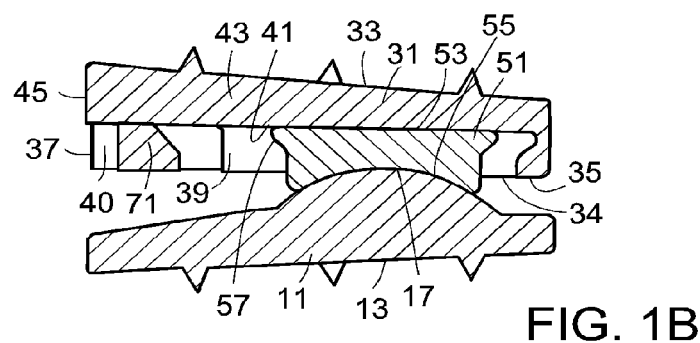
Figure 1C:
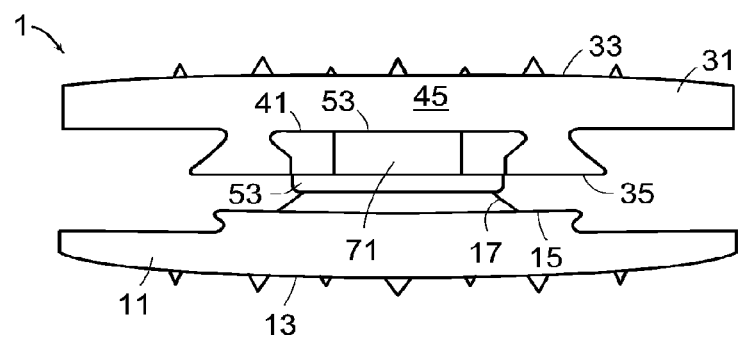

Now referring to FIGS. 1a-1c, there is provided a motion disc 1 comprising:
a) a first prosthetic vertebral endplate 31 comprising:
i) an outer surface 33 adapted to mate with a first vertebral body,
ii) an inner surface 35 having a first opening 34 thereon and a first articulation surface 41,
iii) a body portion 43 connecting the inner and outer surfaces and defining a sidewall 45 comprising a second opening 37 thereon,
b) a second prosthetic vertebral endplate 11 comprising:
i) an outer surface 13 adapted to mate with a second vertebral body, and
ii) an inner surface 15 comprising a first articulation surface 17,
c) a core member 51 comprising:
i) a first articulation surface 53 adapted for articulation with the first articulation surface of the first endplate, and
ii) a second articulation surface 55 adapted for articulation with the first articulation surface of the second endplate,
wherein the first and second openings communicate to form a channel 39 having a first open end 40, and wherein the core member is disposed within the channel and oriented therein to produce a first articulation interface between the first articulation surface of the first endplate and the first articulation surface of the core member, and a second articulation interface between the first articulation surface of the second endplate and the second articulation surface of the core member.

The motion disc of FIGS. 1a-1c further comprises means for limiting the translation of the core member. In FIGS. 1a-1c, the means comprises a locking tab 71 that is adapted to securely lock into place after the core has been inserted and to help retain the core within the channel.

Now referring to FIGS. 1a-1c, in some embodiments, the device comprises four main components: an inferior endplate 11, a superior endplate 31, a core member 51, and a locking tab 71. In one preferred embodiment, the inferior endplate comprises a substantially convex surface 17 that is designed to conform to and mate with a substantially concave surface 55 formed in the core member. The superior endplate has an open channel 39 within which substantially flat lower articulation surface 41 is disposed. The substantially flat lower articulation surface 41 is intended to mate with the substantially flat upper articulation surface 53 of the core member. Channel 39 is designed to retain the core and prevent its lateral expulsion. The core member comprises a substantially concave bottom articulation surface 55 and a substantially flat top articulation surface 53, each of which is designed to mate with the corresponding surfaces on the endplates to form articulation interfaces. Preferably, the articulation interfaces are conforming. In addition, the core member is designed with a retaining feature 57 that mates with a corresponding undercut formed in the sidewall, thereby promoting its retention within the superior endplate channel. Lastly, the locking tab 71 is designed to effectively close the open end of the channel once the core member has been inserted, thereby promoting retention of the core.

In other embodiments, the features on the superior and inferior endplates can be reversed. For example, the substantially flat articulation surface of the superior endplate could be provided upon the inferior endplate, and the substantially curved surface of the inferior endplate could be provided on the superior endplate. In addition, the placement of the ball and socket-like substantially curved surfaces could be reversed so that the core member has a substantially convex articulation surface and the corresponding endplate has a matching substantially concave articulation surface. The substantially flat articulation surfaces may also be modified to be slightly curved and still provide substantially translational motion. Lastly, additional components such as screws for initial fixation of the implant may be added to the design.

Each of the four main components of one preferred embodiment will now be described in more detail:

Now referring to FIGS. 2a-2d, in one embodiment, inferior endplate 11 has an inferior surface 13 designed to mate with a natural vertebral endplate, a superior surface 15 designed to mate with both instrumentation and the core member, and a body portion 16 therebetween. The periphery of the inferior endplate comprises an anterior wall 21, a posterior wall 23, and sidewall portions 25 and 27.

Preferably, the inferior (outer) surface 13 of this endplate is either flat, curved or domed to match the natural vertebral endplate. Alternatively, the geometry of the inferior surface can be designed so that it will match the shape of the patient's vertebral endplate after the vertebral endplate has been modified by an endplate-shaping instrument. In addition, the inferior surface of this endplate can further comprise features to promote and secure initial fixation and bony ingrowth including, but not limited to, spikes, keels, teeth, projections (such as dovetails), recesses (such as grooves) and porous coatings.

Superior (inner) surface 15 comprises a peripheral portion 9 and a raised inner portion 7 extending substantially from the middle of the peripheral portion. This raised inner portion comprises a raised surface 5, a sloped anterior wall 3, and a pair of raised sidewalls 2,4.

Extending from the raised surface of the superior surface of the inferior endplate is a highly polished substantially convex articulation surface 17 designed to mate with a corresponding substantially concave articulation surface (not shown) disposed upon the core member. Preferably, substantially convex articulation surface 17 is further designed to conform to the corresponding concave articulation surface. In the preferred embodiment the articulation surface 17 is convex. However, the substantially curved articulation surface can also be concave if desired to mate with a corresponding substantially convex articulation surface (not shown) disposed upon the core member. Preferably, the substantially curved articulation surface 17 has been polished to a surface roughness Ra of no more than 10 nm.

Preferably, formed upon each raised sidewall is a slotted guide rail 60 running substantially along the length of each raised sidewall. For the purposes of the present invention, a slot is a longitudinally-extending recess in a first surface having a continuous opening onto a second lateral surface along at least a portion of its longitudinal axis. In contrast, a hole is closed about its periphery along its longitudinal axis and so does not open onto a second lateral surface. In some embodiments particularly suited for anterior approaches, the rails run in an anterior-posterior direction. These two guide rails are designed to mate with instrumentation used during the surgical procedure, and optionally with additional implant components (such as a revision spacer or a locking tab). When used as guide rails, slots formed in the raised side walls are more advantageous to holes running through the raised portion because a hole disposed near the edges of the raised portion would be prone to failure and so additional material would be required to support the raised sidewall. In preferred embodiments, the inner surface of the slot is angled. Without wishing to be tied to a theory, it is believed that angled slots are often selected over square slots because a square slot disposed near the edges of the raised portion is prone to failure and so additional material is required to support the raised sidewall. Preferably, the guide rails are located within the footprint of the disc formed by the side wall portions 25 and 27 of the endplates.

Therefore, in accordance with the present invention, there is provided an intervertebral motion disc comprising:
a) a first motion segment comprising:
   i) an outer surface adapted to mate with a first vertebral body,
   ii) an inner surface comprising a first articulation surface,
   iii) a front and a back wall between the inner and outer surfaces, and
   iv) a pair of slots formed in the first motion segment, each slot running substantially from the front wall and opening onto the front wall,
b) a second motion segment comprising:
   i) an outer surface adapted to mate with a second vertebral body,
   ii) an inner surface comprising a first articulation surface, and
wherein the articulation surfaces are adapted to produce an articulation interface.

In other embodiments particularly suited for translateral approaches, the rails run at a substantial angle to the anterior-posterior direction. Typically, this substantial angle is between about 30 and about 60 degrees from the anterior-posterior direction.

Now referring to FIGS. 3a-3c, superior endplate 31 has a superior outer surface 33 designed to mate with the vertebral endplate, an inferior inner surface 35a and 35b that is designed to mate with both instrumentation and the core member, and a body portion 43 therebetween defining a plurality of sidewalls, including an anterior wall 45, a posterior wall 46, and lateral wall portions 47 and 48.

Preferably, the superior outer surface 33 of this endplate is either flat, curved or domed to match the natural vertebral endplate. Alternatively, the geometry of the superior surface can be designed so that it will match the shape of the patient's vertebral endplate after the vertebral endplate has been modified by an endplate-shaping instrument. In addition, the superior surface of this endplate can further comprise features to promote secure initial fixation and bony ingrowth including, but not limited to, spikes, keels, teeth, projections (such as dovetails), recesses (such as grooves) and porous coatings.

Now referring also to FIGS. 1a-1c, channel 39 is formed from the communication of the second opening 37 in the anterior wall with the first opening 34 formed on inner surface 35a of this endplate. In this embodiment, the channel has i) a substantially flat articulation surface 41 that provides linear translation and is designed to mate with a corresponding substantially flat articulation surface of the core member and ii) a sidewall 50 surrounding three sides of the substantially flat articulation surface. Preferably, substantially flat articulation surface 41 is further designed to conform to a corresponding substantially flat articulation surface of the core member. In some embodiments, the substantially flat articulation surface 41 may be replaced with a slightly curved articulation surface. Preferably, the substantially flat articulation surface has been polished to a surface roughness Ra of no more than 10 nm. The channel has a width adapted to receive and retain the core. Preferably, the channel has a shape that allows the core to be easily inserted therein and then retained therein by a means for limiting translation. In the preferred embodiment, the sidewall 50 of the channel has an angular undercut 46 formed therein that is designed to retain the core.

In some embodiments (as in FIGS. 1a-1c), bottom surface 41 is substantially flat to provide substantially translational motion with a corresponding flat superior surface of the core member. However, in other embodiments, this bottom surface is slightly curved to provide not only substantially translational motion with a corresponding slightly curved superior surface of the core member, but also a soft resistance to extreme A-P translation of the core. Preferably, the slightly curved interface is hemicylindrical, preferably with the curve of the hemicylinder running in the anterior-posterior ("A-P") direction. In other embodiments, the curve of the hemicylinder runs in the medial-lateral ("M-L") direction, and so allows the use of a thicker core member.

The opened end channel of FIGS. 1a-1c and 3a-3c is believed to be novel in prosthetic intervertebral motion discs having an intermediate component disposed between a pair of prosthetic vertebral endplates. The open end of the channel is advantageous in that it allows the surgeon to insert only the upper and lower plates into the disc space, and then insert the intermediate piece through the open end of the channel. Because the combination of the upper and lower endplates can be inserted with a lower profile than if the intermediate component were in place, there is a lesser need to severely overdistract or otherwise harm the opposing natural vertebral endplates. The substantially translational articulation capability provided by the first articulation interface allows the disc to more nearly imitate the natural motion of an intervertebral disc.

Therefore, in accordance with the present invention, there is provided a method of implanting an intervertebral motion disc, comprising the sequential steps of:
  inserting into a disc space a partial motion disc comprising:
    a) a first prosthetic vertebral endplate comprising:
      i) an outer surface adapted to mate with a first vertebral body, and
      ii) an inner surface comprising a first motion surface,
    b) a second prosthetic vertebral endplate comprising:
      i) an outer surface adapted to mate with a second vertebral body,
      ii) an inner surface comprising an opening forming a channel comprising opposing side walls, a first open end and a second motion surface, and
  inserting into the open end of the channel a core member comprising:
    i) a first surface adapted for motion with the first motion surface, and
    ii) a second surface adapted for motion with the second motion surface, wherein the core member is disposed within the channel and oriented therein to provide a first motion with the first motion surface and a second motion with the second motion surface.

Figure 4:
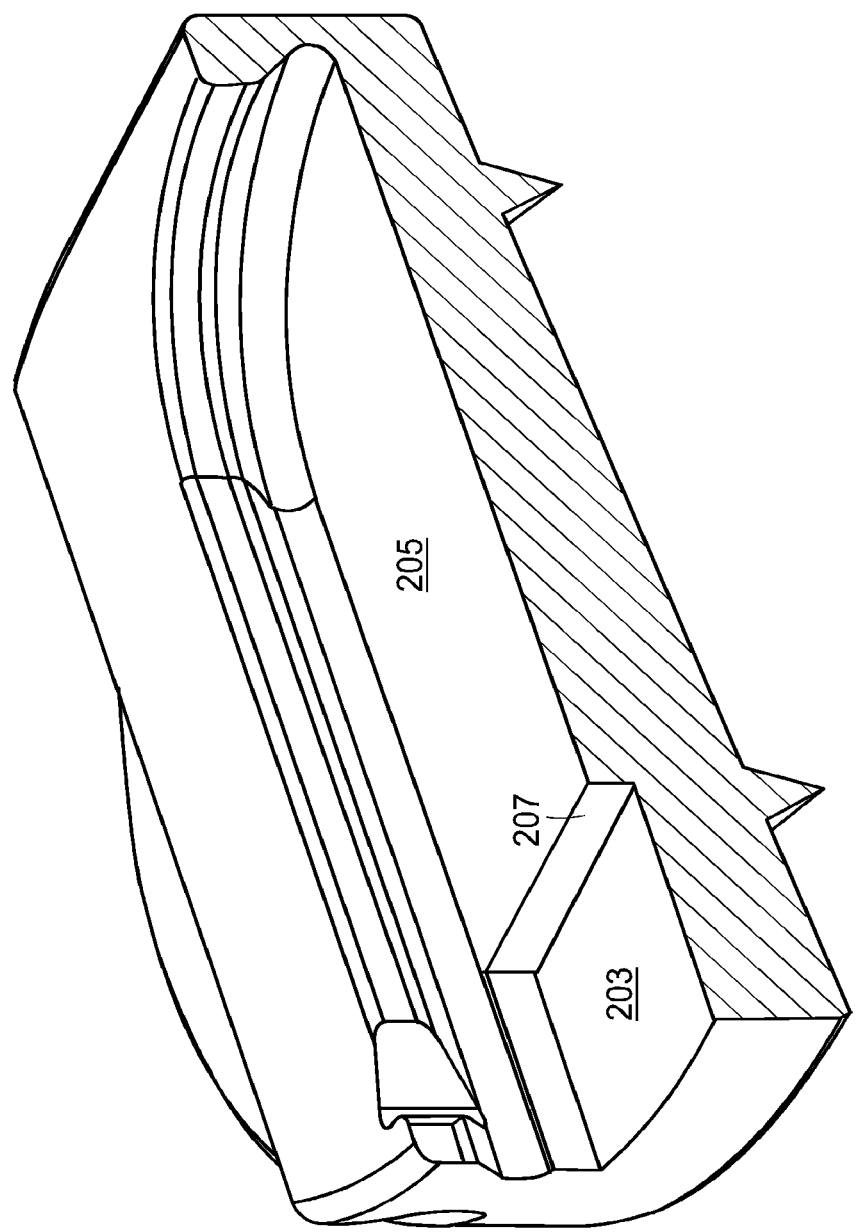
FIGS. 4, 5, and 6 disclose embodiments cross-sectioned through the channel of an endplate.

In some embodiments, now referring to FIG. 4, the channel comprises a sunken anterior surface 203 and a raised posterior articulation surface 205. Because these surfaces occupy different levels, the raised posterior portion can now be more easily polished. In some embodiments, the transition between these surfaces defines a ledge 207. This ledge acts as a stop against overinsertion of the tab, thereby preserving the high polish of the raised posterior articulation surface, and eases insertion of the core.

Figure 5:
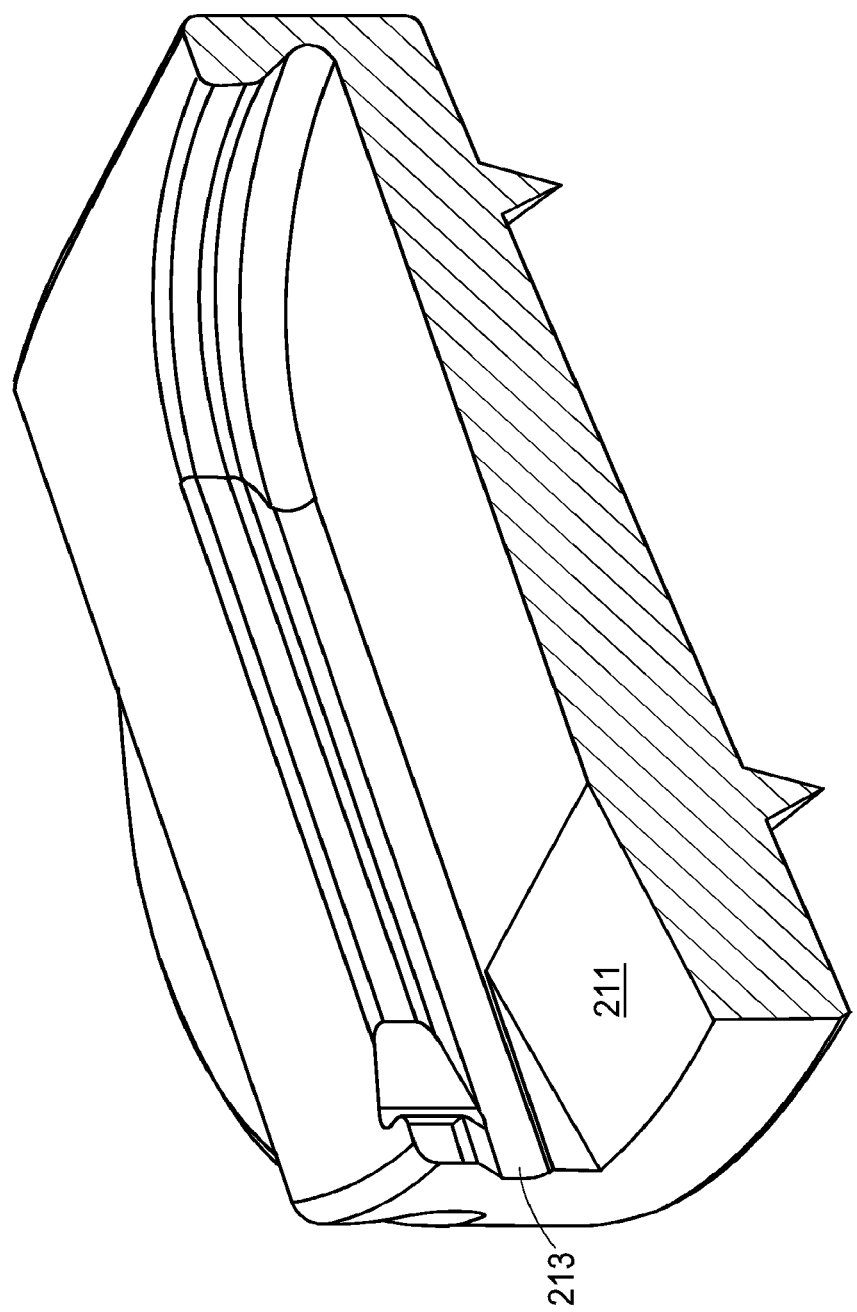

In some embodiments, now referring to FIG. 5, the anterior surface 211 is ramped to rise posteriorly. This embodiment also minimizes the necessary polishing of the articulation surface. As the tab moves up the ramp, the combined action of the elevation rise and the elevation limit provided by the undercut dovetail 213 of the sidewall acts as a stop upon the further posterior movement of the tab.

When the patient is standing in a supine position, the natural loads upon the spine are such that the core member is most preferably positioned in the posterior portion of the motion disc, as in FIGS. 1a-1c, and more preferably between about 60-80% towards the posterior. When the patient first bends forward, the core member may move anteriorly or posteriorly. If the core moves anteriorly, when the patient returns to a supine position, the substantially flat nature of the channel of FIGS. 1a-1c does not help the core member move back to its original posterior position.

Figure 6:
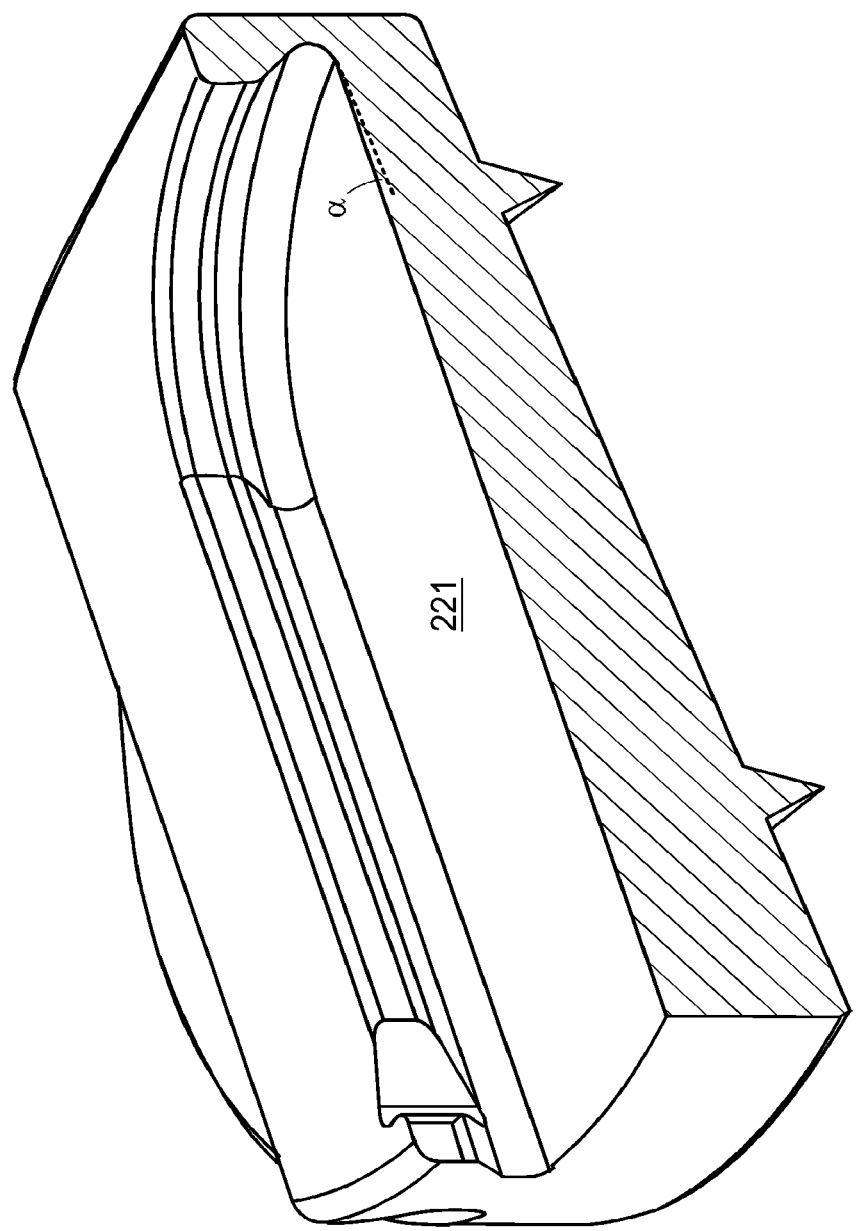

Therefore, in some embodiments, now referring to FIG. 6, at least a portion of the channel is ramped to slope downward posteriorly. The channel of FIG. 6 comprises an anterior articulation surface having a downward sloping ramp 221. If the core is disposed in an anterior portion of the channel, the non-parallel nature of the bearing surfaces will urge the core to move back to its original posterior position when the patient returns to an erect position.

Therefore, in accordance with the present invention, there is provided a prosthetic vertebral endplate, comprising:
  i) an outer surface adapted to mate with a first vertebral body to define a first attachment plane substantially parallel to the vertebral body endplate, and
  ii) an inner surface comprising a substantially flat motion surface, wherein the substantially flat motion surface and the first attachment plane define an angle α. In one preferred embodiment, the angle α of the ramp is between about 10 and about 30 degrees.

When the channel of the present invention contains a substantially flat articulation surface, overdistraction caused by insertion of the core member is desirably minimized. However, in other embodiments, the channel may include a slightly curved surface which rises anteriorly and/or a flat surface having an anteriorly-disposed lip having a height less than that of sidewalls. Since the lip or slightly curved surface may desirably retain the core member within the channel, it is contemplated that such a lip may obviate the need for another translation-limiting limiting component such as a tab that prevents expulsion of the core while still providing a height reduction benefit that lessens the need for overdistraction. Preferably, this lip has a height that is no more than 80% of the channel depth, more preferably no more than 50%, more preferably no more than 25%.

Referring again to FIGS. 3a-3c, formed in each sidewall 47, 48 is a recessed guide rail 49. Guide rail 49 begins at the anterior wall, extends across each sidewall, and ends at the posterior wall. These two guide rails correspond to the two guide rails 60 of the inferior plate.

Figure 7A:
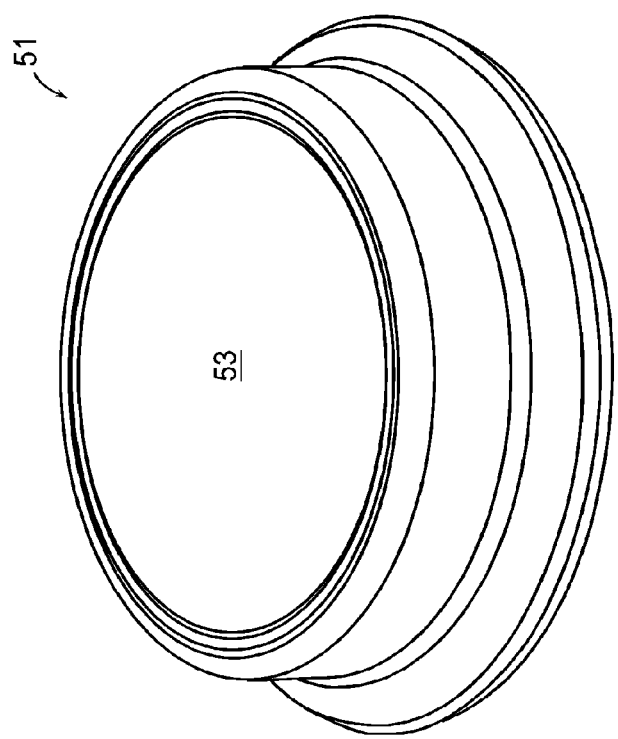
FIGS. 7a, 7b, and 7c disclose isometric, cross-sectional and front views of the core member of the first embodiment of the present invention.
Figure 7C:
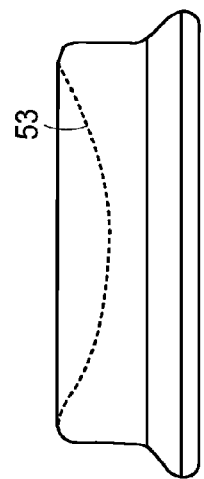
Figure 7B:
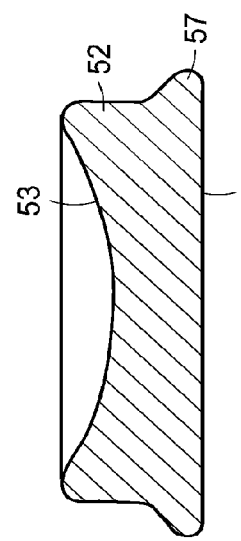

Now referring to FIGS. 7a-7c, the core member 51 comprises a body portion 52 forming a substantially flat superior surface 55 that is designed to articulate with the bottom surface of the superior endplate and a substantially curved inferior surface 53 that is designed to mate with the inferior endplate. In some preferred embodiments, the body portion has a substantially cylindrical body portion 52. In some preferred embodiments, the body portion has a substantially rectangular body portion 52. Preferably, superior surface 55 is further designed to conform to the bottom surface 41 of the superior endplate. Also preferably, substantially curved inferior surface 53 is designed to conform with a corresponding substantially curved upper surface of the inferior endplate. In some embodiments (as in FIGS. 7a-7c), superior surface 55 is substantially flat to provide substantially translational motion with a corresponding flat bottom surface of the superior endplate. However, in other embodiments, superior surface 55 is slightly curved to provide substantially translational motion with a corresponding curved bottom surface of the superior endplate as well as soft resistance to extreme translational motion.

The substantially curved inferior surface can be any shape designed for pivotal articulation, including hemispherical, hemicylindrical, hemi-ellipsoidal, and oblong. However, in preferred embodiments, the curved surface is hemi-spherical. In the preferred embodiments, the substantially curved inferior articulation surface of the core is concave. However, the curved articulation surface can also be convex, if desired, to mate with a corresponding substantially concave articulation surface disposed upon an endplate.

The substantially flat superior surface may be modified to any slightly curved geometry that allows at least one degree of substantially translational motion, including a hemi-cylindrical shape.

In addition to the two articulation surfaces, the core has a peripherally disposed retaining feature 57 that is designed to prevent the core from accidentally dislocating from the implant. The shape of the retaining feature is adapted to fit a complementary feature (46 of FIGS. 3*a*-3*c*) in the sidewall of the retaining channel. In this embodiment, the retaining feature 57 extends from the cylindrical body portion. In a preferred embodiment, the retaining feature is an angled flare disposed near the end of the core having the substantially translational surface. However, in other embodiments, the retaining feature can be a recess extending into the body portion 52.

Typically, the core of a conventional motion disc has either two convex surfaces or two concave surfaces. The Germain motion disc is the only motion disc known to the present inventors in which the core comprises one convex motion surface and one concave motion surface. However, Germain further requires the radius of the upper surface to be smaller than the radius of the lower motion surface. Without wishing to be tied to a theory, because of this requirement, the Germain disc may suffer from a high center of rotation.

In an effort to overcome these deficiencies, in some embodiments of the present invention, the radius of the upper surface of the core is greater than the radius of the lower motion surface. Without wishing to be tied to a theory, this embodiment of the present invention may possess an advantage of a low center of rotation.

Therefore, in accordance with the present invention, there is provided an intervertebral motion disc comprising:
 a) an upper prosthetic vertebral endplate comprising:
  i) an outer surface adapted to mate with an upper vertebral body,
  ii) an inner surface having a first articulation surface,
 b) a lower prosthetic vertebral endplate comprising:
  i) an outer surface adapted to mate with a lower vertebral body, and
  ii) an inner surface having a first articulation surface, and
 c) a core member comprising:
  i) an upper articulation surface adapted for articulation with the first articulation surface of the upper endplate and having a radius, and
  ii) a lower articulation surface adapted for articulation with the first articulation surface of the lower endplate and having a radius,
wherein the core member is disposed between the endplates and oriented therein to produce an upper articulation interface between the first articulation surface of the upper endplate and the upper articulation surface of the core member, and a lower articulation interface between the first articulation surface of the lower endplate and the lower articulation surface of the core member, and
wherein the radius of the upper articulation surface of the core member is greater than the radius of the lower articulation surface of the core member.

Preferably, the radius of the upper motion surface of the core is at least three times greater than the radius of the lower motion surface of the core, more preferably between 3 and 5 times greater. Preferably, the radius of the upper surface of the core is between about 40 mm and about 100 mm, and the radius of the lower motion surface is between about 10 mm and about 30 mm. Preferably, the radius of the upper surface of the core is between 40 mm and 80 mm. Below 40 mm, the depth of the curve requires adding significantly more material to the corresponding endplate, thereby increasing the height of the implant. Above 80 mm, the curve provides a less significant braking.

Typically, the core of a conventional motion disc has either one flat surface and one curved surface (as in Erickson, Yuan and Bullivant), two cylindrical surfaces (as in Charite '766), or two hemispherical surfaces (as in Germain). However, a substantially flat surface in a motion disc does not resist extreme movement of the core. Motion discs having two hemicylindrical surfaces can not provide the desired pivotal movement over 360 degrees. Motion discs having two hemispherical surfaces do not allow for the easy correction of misaligned endplates.

In an effort to overcome these deficiencies, in some embodiments of the present invention, the core of the present invention has one hemispherical surface and one non-hemispherical curved surface. Preferably, the non-hemispherical curved surface is hemicylindrical. In this condition, the hemispherical surface provides the pivotal rotation freedom found in the natural disc, while the linear dimension of the hemicylindrical surface (when provided in the medial-lateral direction, as in FIGS. 12 and 22*a*) provides substantially translational movement in a first direction (thereby providing easy correction of misaligned endplates), and curved dimension of the hemicylindrical surface provides some resistance against extreme movement in a second direction.

Therefore, in accordance with the present invention, there is provided an intervertebral motion disc comprising:
 a) a first prosthetic vertebral endplate comprising:
  i) an outer surface adapted to mate with a first vertebral body,
  ii) an inner surface having a first articulation surface,
 b) a second prosthetic vertebral endplate comprising:
  i) an outer surface adapted to mate with a second vertebral body, and
  ii) an inner surface having a first articulation surface, and
 c) a core member comprising:
  i) a first articulation surface adapted for articulation with the first articulation surface of the first endplate, and
  ii) a second articulation surface adapted for articulation with the first articulation surface of the second endplate,
wherein the core member is disposed between the endplates and oriented therein to produce a first articulation interface between the first articulation surface of the first endplate and the first articulation surface of the core member, and a second articulation interface between the first articulation surface of the second endplate and the second articulation surface of the core member, and
wherein the first articulation surface of the core member is spherical and the second articulation surface of the core member is curved and non-spherical.

Also in accordance with the present invention, there is provided a core member for articulation between first and second prosthetic vertebral endplates, comprising:
 i) a first articulation surface adapted for articulation with a first articulation surface of the first prosthetic vertebral endplate, and
 ii) a second articulation surface adapted for articulation with the first articulation surface of the second prosthetic vertebral endplate, wherein the first articulation surface is a portion of a sphere and the second articulation surface is a portion of a curved, non-spherical shape.

Preferably, the non-spherical curved surface is a hemicylindrical surface, as such a surface that can articulate with a similar opposing hemicylindrical surface and provide conforming articulation. Also preferably, the curved dimension of the hemicylindrical surface is provided in the A-P direction (to provide a soft braking) while the linear dimension is provided in the medial-lateral direction. However, in other embodiments, the curved dimension of the hemicylindrical surface is provided in the medial-lateral direction, while the linear dimension is provided in the anterior-posterior direction.

Also preferably, the hemispherical surface is substantially curved and the curved, non-hemispherical surface is slightly curved.

Figure 8:
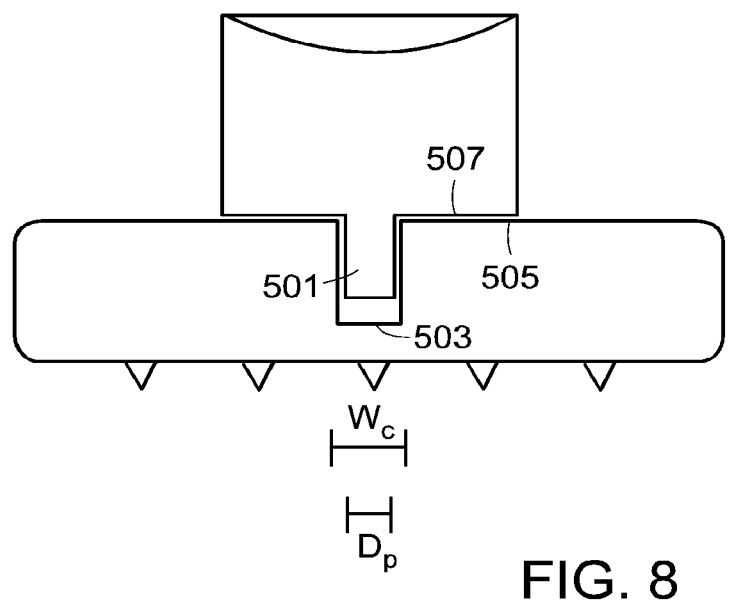
FIG. 8 discloses a cross-section of an embodiment of the present invention in which the core member has a non-articulating projection.

In the embodiment of FIGS. 3a-3c, because the translational articulation surface 41 that mates with the core member is disposed within the channel, both the core retention function and translation surface function of this endplate are provided by the same surface within the channel. However, in other embodiments, the core retention function and translation surface function can be provided by separate surfaces. For example, now referring to FIG. 8, there is provided a motion disc wherein the core member has a projection 501 that extends only partially into channel 503. The channel and projection elements of this device function merely to limit the lateral translational freedom of the core member. In this embodiment, the bottom of the channel does not have to be adapted to support articulation motion. Rather, substantially flat articulation surface 505 provided on the inner surface of the endplate forms an articulation interface with the substantially flat articulation surface 507 of the core member.

Figure 9:
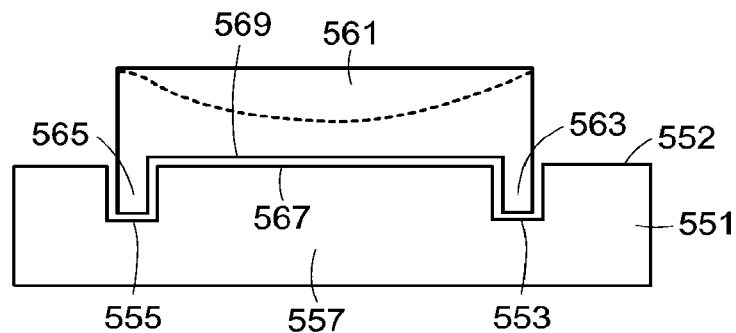
FIG. 9 discloses a cross-section of an embodiment of the present invention in which the core member has two non-articulating projections.

Similarly, in FIG. 9, there is provided a prosthetic vertebral endplate 551 having two channels with an articulation surface therebetween. In particular, endplate 551 comprises an inner surface 552 having first 553 and second 555 channels formed therein, and an articulation surface 567 formed between the channels. The channels begin at the anterior wall 557 of the endplate and terminate prior to opening onto the posterior wall (not shown) of the endplate. Core member 561 comprises first 563 and second 565 projections and an articulation surface 569 therebetween, each projection having a shape that mates with its corresponding channel to limit the medial-lateral translation of the core member. Anterior-posterior translation is accomplished by the mating of articulation surface 569 of the core and articulation surface 567 of the endplate to produce an articulation interface. Expulsion of the core member of this embodiment can be prevented by any number of means. For example, after the core member is slid into the channels, locking tabs can be inserted into the anterior end of each channel. Alternatively, the intermediate portion 567 of the inner surface can comprise at least one flexible tab that allows the passage of the core member towards the posterior portion of the endplate, but prevents its passage back out.

Figure 10:
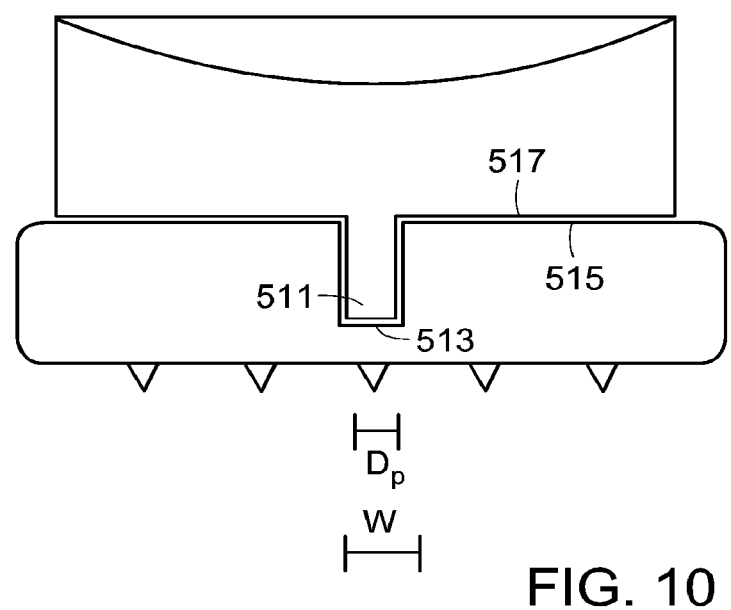
FIG. 10 discloses a cross-section of an embodiment of the present invention in which the core member has an articulating projection.

In other embodiments, the core member and superior endplate can be adapted to provide more than one articulation interface. Now referring to FIG. 10, the bottom surface 511 of the projection is polished and extends sufficiently into the channel to bear upon the bottom surface 513 of the channel to form a first articulation interface, while an articulation surface 515 is also provided on the inner surface of the endplate to form a second articulation interface with a second articulation surface 517 of the core member.

Likewise, in FIG. 9, projections 563,565 may optionally mate with the bottom surfaces of the channels to form additional articulation interfaces.

In preferred embodiments, the core member is adapted to provide pivotal motion with a first endplate. Preferably, the pivotal motion is provided by the corresponding substantially curved surfaces of the core member and a first endplate. More preferably, the curved surfaces are conforming More preferably, the conforming curved surfaces are selected from the group consisting of hemispherical and hemicylindrical surfaces. Still more preferably, the conforming curved surfaces are hemispherical surfaces.

In preferred embodiments, the core member is adapted to provide at least one degree of translation motion with a second endplate. Preferably, the at least one degree of translation motion is provided by corresponding substantially flat planar surfaces of the core member and a second endplate. Now referring to FIG. 11, in some embodiments, exactly one degree of translation motion is achieved by sizing the core member so that its diameter $D_c$ equals the width W of the channel in which it is disposed. In this case, the one degree of freedom is translation in the A-P direction. Now referring to FIG. 10, in other embodiments, one degree of translation motion is realized by sizing a projection upon the core member so that the diameter of the projection $D_P$ equals the width W of the channel in which it is disposed. Preferably, the motion provided by the one-degree-of-freedom embodiment is in the anterior-posterior direction. In other embodiments, more than one degree of freedom may be realized by sizing the core member so that its diameter (or the diameter of its projection that bears upon the articulation surface) is smaller than the width W of the channel, thereby allowing the core to move laterally as well.

Figure 12:
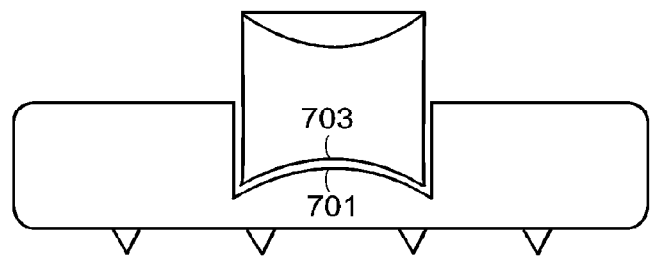
FIG. 12 discloses a cross-section of an embodiment of the present invention in which the translation surface is hemicylindrical.

In other embodiments, as in FIG. 12, one degree of translation motion is realized by providing a channel having a hemicylindrical surface 701 and a core member having a corresponding hemicylindrical surface 703 to produce a hemicylindrical interface. In this particular embodiment, the core has a slightly convex hemicylindrical surface adapted to provide translational motion in the A-P direction with the slightly concave hemicylindrical bottom surface of the channel.

The flat surfaces that provide translation movement in Erickson are either circular or elongated. However, in the circular embodiments, since there is very little medial-lateral movement in natural spinal movement, the circular designs of Erickson do not readily mimic the natural spinal movements. In the elongated embodiments, Erickson teaches that the elongated embodiment provides movement along only one axis. Accordingly, if an elongated (uniaxial) design of Erickson is selected, any misalignment of the components in the M-L axis can not be easily corrected by simple translation of this motion surface.

Therefore, in some embodiments, the core member and its slightly curved or substantially flat translation surface are adapted to provide a translation surface that provides for substantial movement in the A-P axis and lesser movement in the M-L axis. When this embodiment is selected, the device provides not only the degree of A-P movement that substantially mimics the A-P motion of the natural intervertebral disc but also a limited amount of M-L motion that allows the surgeon to use this interface to compensate for any surgical misalignment of the prosthetic vertebral endplates.

Therefore, in accordance with the present invention, there is provided intervertebral motion disc comprising:

a) a first prosthetic vertebral endplate comprising:

i) an outer surface adapted to be attached to a first vertebral body, and
ii) an inner surface comprising a first articulation surface,
b) a core member comprising:
i) a first articulation surface, and
wherein the first articulation surface of the core member and the first articulation surface of the first endplate are adapted to form a first articulation interface having a range of anterior-posterior A-P motion and a range of medial-lateral M-L motion,
wherein the range of A-P motion is between 1.5 and 50 times greater than the range of M-L motion.

Preferably, the maximum range of A-P motion is between 1.5 and 50 times greater than the maximum range of M-L motion, more preferably between 1.5 and 8 times, more preferably between 4 and 8 times, more preferably between 5 and 7 times, and still more preferably between 5.5 and 6.5 times.

In some embodiments designed for use in the lumbar spine, the maximum range of A-P motion is between 2 and 5 mm, preferably between 3 and 4 mm, and the maximum range of M-L motion is between 0.25 mm and 2 mm, preferably between 0.25 mm and 1 mm.

Figure 11:
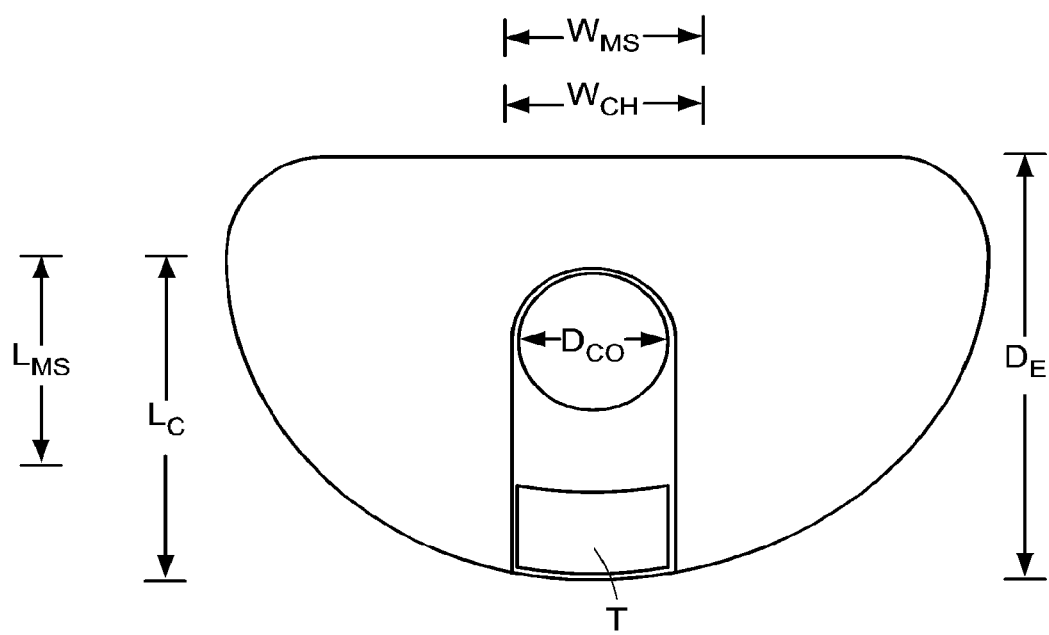
FIG. 11 discloses a cross-section of an embodiment of the present invention which defines distances.

Now referring to FIG. 11, in preferred embodiments, the channel is defined by a length $L_{CH}$ and a width $W_{CH}$, the articulation surface portion of the channel is defined by a length $L_{MS}$ and a width $W_{MS}$, and the core member is defined by a diameter $D_{CO}$. As shown in FIG. 11, the length of the articulation surface does not include the space occupied by a tab T.

Preferably, the length of the articulation surface $L_{MS}$ is between about 10% to about 50% greater than the diameter $D_{CO}$ of the core. When this range is achieved in typical geometries, the core member can move between about 1 mm and about 5 mm in the anterior-posterior direction. Within this range, the core member has translation capability that mimics typical anatomical anterior-posterior motion.

Preferably, the width of the channel $W_{CH}$ is between about 5% and about 20% greater than the diameter $D_{CO}$ of the core. When this range is achieved in typical geometries, the core can move between about 0.5 mm and about 2 mm in the medial-lateral direction. This 0.5-2 mm of freedom may correct for misplacement of the pivotal articulation surface elements.

Preferably, when the channel has a closed end, the length of the channel $L_{CH}$ extends to between about 60% to 80% the distance from the anterior wall to the posterior wall of the endplate. When this range is achieved, the core can reside substantially near the anatomically typical vertical axis of rotation.

In preferred embodiments, each of the inferior endplate, superior endplate and core member is manufactured from a material that possesses the strength and high wear resistance desired for use as a motion disc component.

These components of the present invention may be made from any non-resorbable material appropriate for human surgical implantation, including but not limited to, surgically appropriate metals, and non-metallic materials, such as carbon fiber composites, polymers and ceramics.

If a metal is chosen as the material of construction for a component, then the metal is preferably selected from the group consisting of titanium, titanium alloys (such as Ti-6Al-4V), chrome alloys (such as CrCo or Cr—Co—Mo) and stainless steel. If an articulation interface is formed from first and second metal articulation surfaces, then the components are preferably manufactured so that the grains of the first metal articulation surface are disposed substantially perpendicular to the grains of the second metal articulation surface grains of the first metal articulation surface.

Therefore, in accordance with the present invention, there is provided an intervertebral motion disc comprising:
a) a first prosthetic vertebral endplate comprising:
i) an outer surface adapted to be attached to a first vertebral body, and
ii) an inner surface comprising a first articulation surface comprising a first metal having grains oriented in a first direction, and
b) a core member comprising:
i) a first articulation surface comprising a metal having grains oriented in a second direction,
wherein the first articulation surface of the core member and the first articulation surface of the first endplate are adapted to form a first articulation interface, and
wherein the first and second directions of grain orientation are not parallel.

If a polymer is chosen as a material of construction for a component, then the polymer is preferably selected from the group consisting of polyesters, (particularly aromatic esters such as polyalkylene terephthalates, polyamides; polyalkenes; poly(vinyl fluoride); PTFE; polyarylethyl ketone PAEK; and mixtures thereof.

If a ceramic is chosen as the material of construction for a component, then the ceramic is preferably selected from the group consisting of alumina, zirconia and mixtures thereof. It is preferred to select an alumina-zirconia ceramic, such as BIOLOX Delta™, available from CeramTec of Plochingen, Germany. Depending on the material chosen, a smooth surface coating may be provided thereon to improve performance and reduce particulate wear debris.

The present inventors believe that metal-ceramic interfaces will provide the best resistance to wear. Accordingly, in particularly preferred embodiments, there is provided an intervertebral motion disc comprising:
a) a first prosthetic vertebral endplate comprising:
i) an outer surface adapted to mate with a first vertebral body, and
ii) an inner surface comprising a first articulation surface comprising a non-ceramic material
b) a core member comprising:
i) a first articulation surface comprising a ceramic, and
wherein the first articulation surface of the core member and the first articulation surface of the first endplate are adapted to form a first articulation interface.

More preferably, the second articulation interface will also have a corresponding ceramic-metal interface.

In some preferred embodiments, the entire core member consists essentially of a ceramic, preferably a sintered polycrystalline ceramic. Preferably, the sintered polycrystalline ceramic comprises at least 50 wt % of a material selected from the group consisting of alumina, zirconia, and alumina-zirconia mixtures. In some alumina-zirconia mixture embodiments, the ceramic comprises 10-30 wt % alumina.

In some alumina-zirconia mixture embodiments, the ceramic comprises 70-90 wt % alumina. In some embodiments, the ceramic comprises alumina having a median grain size of no more than 5 micron, preferably less than 3 microns, more preferably less than 2 microns, more preferably less than one micron. In some embodiments, the ceramic comprises tetragonal zirconia having a median grain size of no more 2 microns, more preferably less than one micron. In some embodiments, the ceramic comprises alumina made from a seeded gel process.

In some embodiments, the core member is polyethylene.

In some preferred embodiments, the first endplate consists essentially of a metallic material, preferably a titanium alloy or a chrome-cobalt alloy. In some preferred embodiments, the second endplate consists essentially of the same metallic material as the first plate.

In some embodiments, the articulation surfaces of the endplates may be coated with a wear-resistant coating, such as diamond film, in order to reduce wear.

In some embodiments, the endplates are made of a stainless steel alloy, preferably BioDur® CCM Plus® Alloy available from Carpenter Specialty Alloys, Carpenter Technology Corporation of Wyomissing, Pa.; and the core member is made of polyethylene, preferably Marathon™ available from DePuy Orthopaedics of Warsaw, Ind. In some embodiments, the endplate articulation surfaces are coated with a sintered beadcoating, preferably Porocoat™ available from DePuy Orthopaedics of Warsaw, Ind.

In some embodiments, the endplates are made from a composite comprising carbon fiber. Composites comprising carbon fiber are advantageous in that they typically have a strength and stiffness that is superior to neat polymer materials such as a polyarylethyl ketone PAEK.

Therefore, in accordance with the present invention, there is provided an intervertebral motion disc comprising:
 a) a first prosthetic vertebral endplate comprising:
  ]i) an outer surface adapted to be attached to a first vertebral body, and
  ii) an inner surface comprising a first articulation surface comprising a composite comprising carbon fiber, and
 b) a core member comprising:
  i) a first articulation surface comprising a metal, wherein the first articulation surface of the core member and the first articulation surface of the first endplate are adapted to form a first articulation interface.

Also in accordance with the present invention, there is provided an intervertebral motion disc comprising:
 a) a first prosthetic vertebral endplate comprising:
  i) an outer surface adapted to be attached to a first vertebral body,
  ii) an inner surface comprising a first articulation surface, and
  iii) a body portion therebetween comprising carbon fiber, and
 b) a core member comprising:
  i) a first articulation surface,
wherein the first articulation surface of the core member and the first articulation surface of the first endplate are adapted to form a first articulation interface.

Preferably, the composite comprising carbon fiber further comprises a polymer. Preferably, the polymer is a polyarylethyl ketone PAEK. More preferably, the PAEK is selected from the group consisting of polyetherether ketone PEEK, polyether ketone ketone PEKK and polyether ketone PEK. In preferred embodiments, the PAEK is PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present as chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises:

a) 40-99% (more preferably, 60-80 vol %) polyarylethyl ketone PAEK, and
 b) 1-60% (more preferably, 20-40 vol %) carbon fiber,
wherein the polyarylethyl ketone PAEK is selected from the group consisting of polyetherether ketone PEEK, polyether ketone ketone PEKK and polyether ketone PEK.

In some embodiments, the composite consists essentially of PAEK and carbon fiber. More preferably, the composite comprises 60-80 wt % PAEK and 20-40 wt % carbon fiber. Still more preferably the composite comprises 65-75 wt % PAEK and 25-35 wt % carbon fiber.

If both the core and endplates are made of materials having a significantly high stiffness, then the device may not fully mimic the shock absorbing function of the natural intervertebral disc.

Therefore, in order to augment the shock absorbing function of the core member, in some embodiments, the core member comprises a shock-absorbing component characterized by a specified range of a spring constant.

Therefore, in accordance with the present invention, there is provided intervertebral motion disc comprising:
 a) a first prosthetic vertebral endplate comprising:
  i) an outer surface adapted to be attached to a first vertebral body, and
  ii) an inner surface comprising a first articulation surface, and
 b) a core member comprising a stiff component and a shock absorbing component having a spring constant of between 500 N/mm and 1000 N/mm, and comprising:
  i) a first articulation surface, wherein the first articulation surface of the core member and the first articulation surface of the first endplate are adapted to form a first articulation interface.

In some embodiments, the core member comprises a stiff component and a shock-absorbing component, and the shock-absorbing component has a spring constant of between about 500 N/mm and 1000 N/mm and a thickness of between 1 mm and 5 mm. When the shock-absorbing component is so designed, it can absorb between about 1000N and 2000 N of load.

In some embodiments, the shock absorbing function of the core is provided by a spring within the core member. Therefore, in accordance with the present invention, there is provided a core member for articulation between first and second prosthetic vertebral endplates, comprising:
  i) a first portion having a first articulation surface adapted for articulation with a first articulation surface of the first prosthetic vertebral endplate,
  ii) a second portion having a second articulation surface adapted for articulation with a first articulation surface of the second prosthetic vertebral endplate, and
  iii) a spring portion disposed between the first and second portions.

Figure 13:
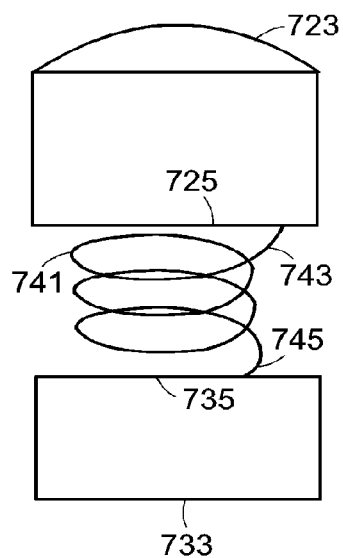
FIG. 13 discloses a side view of a core member having a spring portion.
Figure 14:
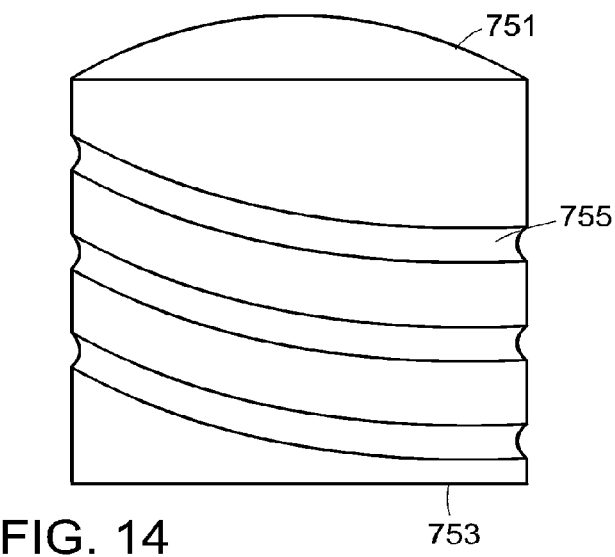
FIG. 14 discloses a side view of a core member having a helical recess therein.

Now referring to FIG. 13, in some embodiments, the spring may be provided by simply manufacturing upper and lower halves of a core member, and then attaching the opposite ends of a compression spring to the opposite ends of the core halves. For example, in FIG. 18, upper core half 721 comprises a first articulation surface 723 and a lower attachment surface 725, while lower core half 731 comprises a second articulation surface 733 and an upper attachment surface 735. Compression spring 741 comprises upper end 743 and lower end 745, wherein the upper end 743 is attached to the lower attachment surface 725 of the upper core half, and the lower end 745 is attached to the upper attachment surface 735 of the lower core half Now referring to FIG. 14, in other embodiments, the spring action is provided by first providing an integral core member having opposing articulation surfaces 751,753 and then shaping the surface of the intermediate portion of the core member with a cutting tool to provide at least one recess 755 therein that provides the spring effect. In some embodiments, the intermediate surface comprises multiple recesses spaced to provide the spring effect. In other embodiments, a helical recess is provided, as in FIG. 14. In other embodiments, the helical recess is made by using a wire and a spinning fixture to produce a deep helical slit in the core member.

Figure 15B:
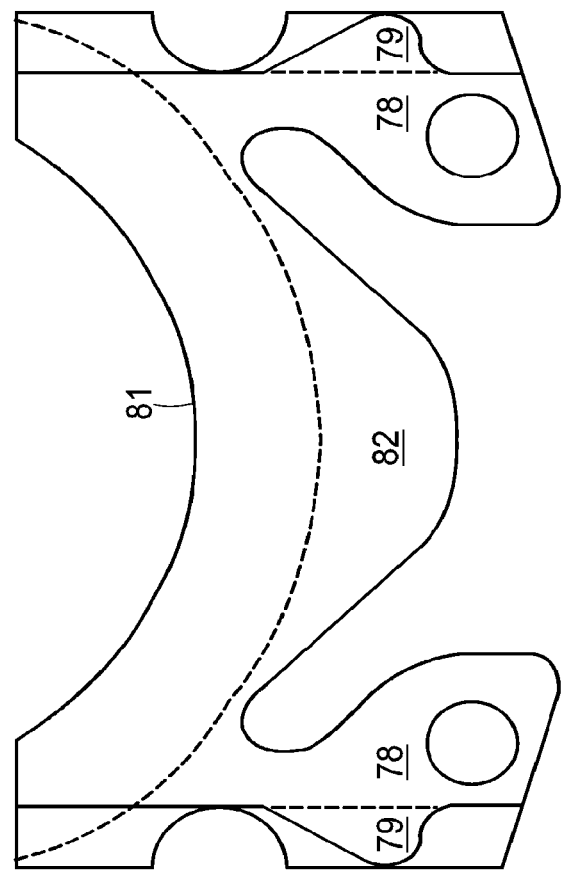
FIGS. 15a-15b disclose isometric and elevated views of the locking tab of the first embodiment of the present invention.
Figure 15A:
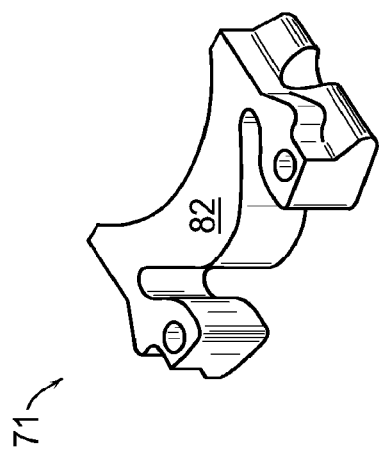

Now referring to FIGS. 15a-15, the locking tab 71 is adapted to securely lock in the channel after the core member has been inserted and to retain the core member within the channel. In one preferred embodiment, the locking tab comprises a body portion 82 having deformable arms 78 extending therefrom and oriented substantially parallel to each other to fit within the channel of the superior endplate. Each arm 78 further comprises a laterally extending wing 79. Because the wingspan defined by the wings is greater than the width of the channel, the arms are deflected inwards as the tab is slid into the retaining channel. These wings are further designed to fit within sockets 32 (of FIGS. 3a-3c) laterally disposed within the channel so that the deflected arms can move back to their original parallel orientation when the wings are accepted by the channel sockets, thereby locking tab securely in place.

The locking tab should be manufactured from a material with the requisite elasticity such as stainless steel, plastic, or nitinol. However, in some embodiments, the elasticity of the locking tab may be relatively low, thereby making it difficult to provide the snap-in function. Accordingly, in some embodiments, the locking means is fastened to the prosthetic vertebral endplate by a fastener such as a screw or anchor.

In preferred embodiments, the locking tab is sized so as to allow the core member to move in the A-P direction. However, in other embodiments, the locking tab may be sized so as to substantially prevent any A-P movement of the core member.

Figure 16:
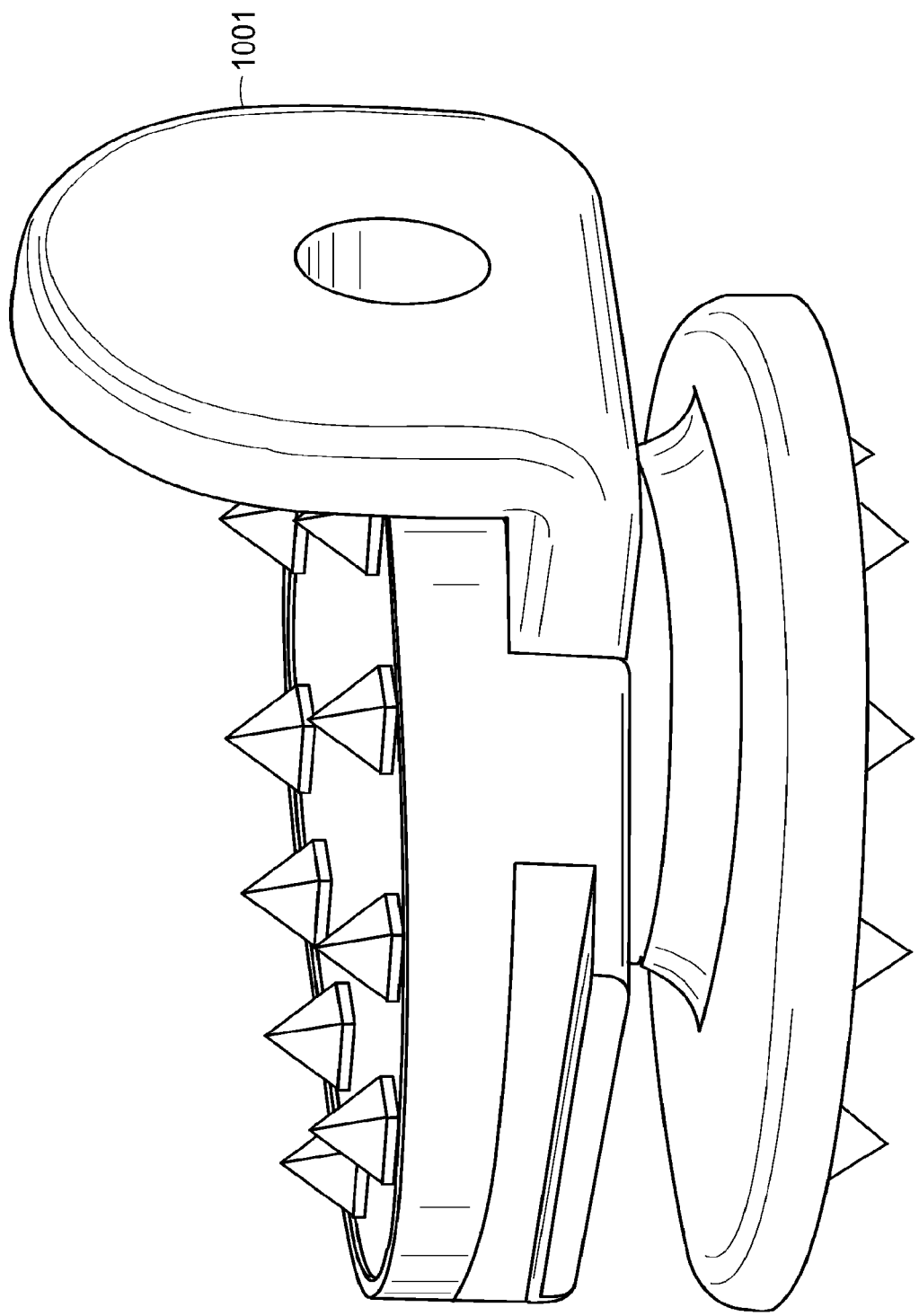
FIG. 16 discloses a locking tab adapted for engagement with a vertebral body.

Now referring to FIG. 16, in some embodiments, the locking tab further comprises an attachment portion 1001 extending from the body of the tab and adapted to attach to a patient's vertebral body. The attachment portion provides an opportunity for short term fixation of the motion disc within the disc space.

In other embodiments, the means for limiting translation comprises:
a) a pin and slot arrangement (preferably spring loaded) wherein the slot runs in the direction of the channel,
a sliding door disposed near the first opening, and
c) a hinged door disposed near the first opening.

In some embodiments, the means for limiting translation comprises a third component shaped to be inserted into the channel from the direction of the inner surface of the endplate.

Now referring to FIGS. 15a-15b, in some embodiments, the tab is provided with an inner surface 81 adapted to mate with the outer surface of the core member. In preferred embodiments, the inner surface of the tab is concave and substantially hemispherical.

Figure 17:
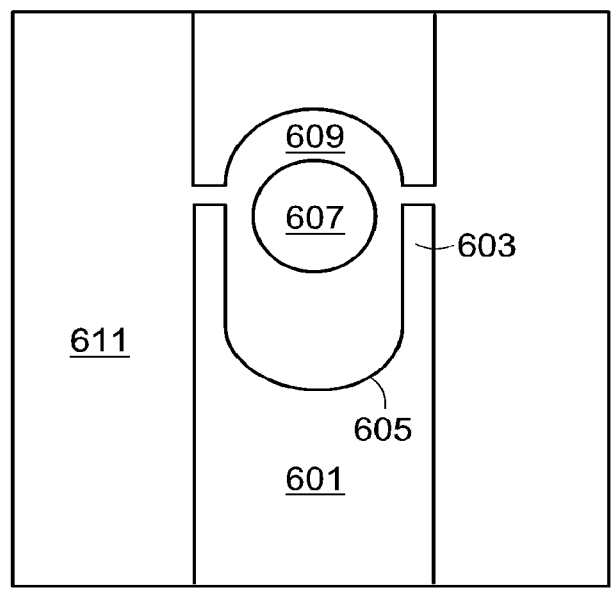
FIG. 17 discloses an elevated view of an endplate, core and tab, wherein the inner surface of the tab has an elongated portion.

In some embodiments, the inner surface of the tab can be further shaped so as to provide substantial translational motion. Now referring to FIG. 17, the tab 601 comprises an inner surface having an elongated portion 603 and a hemispherical portion 605, wherein the elongated portion allows for substantial translation of the core 607 therein. In this case, the channel 609 formed within the inner surface of the endplate 611 can be relatively short. In other embodiments, the channel formed within the inner surface of the endplate can be simply a back wall. The tab of this embodiment can be affixed to the endplate by any conventional means.

Therefore, in accordance with the present invention, there is provided an intervertebral motion disc comprising:
a) a first prosthetic vertebral endplate comprising:
  i) an outer surface adapted to be attached to a first vertebral body, and
  ii) an inner surface comprising:
    a first articulation surface, and
    a raised portion extending from the inner surface substantially adjacent the first articulation surface and having first and second ends, and
b) a removable tab having first and second ends,
wherein the tab is attached to the endplate and oriented so that the first end of the raised portion is substantially adjacent the first end of the tab, and the second end of the raised portion is substantially adjacent the second end of the tab to form an enclosure which substantially encloses the first articulation surface.

Figure 18:
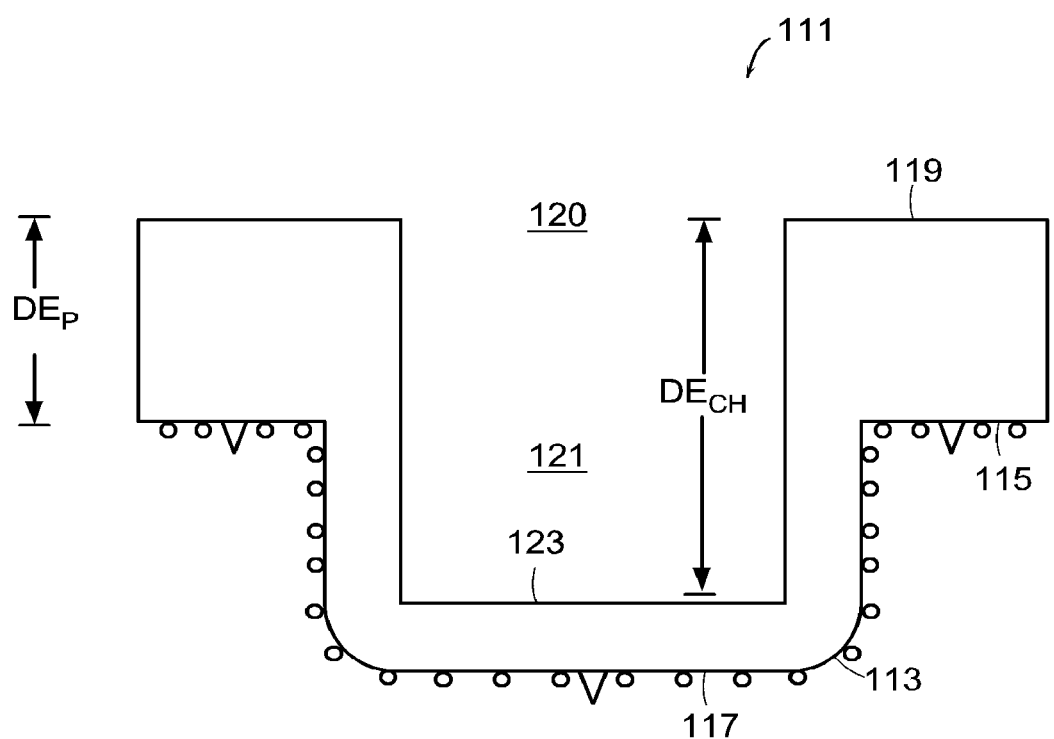
FIG. 18 discloses a cross-section of a superior endplate having a sunken channel.

Now referring to FIG. 18, in some embodiments, the translation surface of the retaining channel is disposed below the level of peripheral surface 115 of the prosthetic vertebral endplate. In this case, the interior portion of the outer surface of the endplate forms a keel to promote the initial and long-term stability of the device, and the translation surface 123 of the retaining channel is contained within the keel. In addition, this embodiment allows the translation surface of the core member to contact the translation surface 123 of the endplate at a much lower location. Therefore, either the overall height of the device could be reduced (thereby allowing for easier insertion of the core member) or the height of the core member could be increased (to provide increased strength). In addition, the large surface area of the keel could be porous coated to promote bony ingrowth.

Therefore, in accordance with the present invention, there is provided a prosthetic vertebral endplate 111 comprising:
  i) an outer surface 113 having a peripheral portion 115 and an interior portion 117, each portion being adapted to be attached to a vertebral body, and
  ii) an inner surface 119 comprising an opening 120 forming a channel 121 defining a channel depth $DE_{CH}$, wherein the peripheral portions of the inner and outer surfaces define a peripheral depth $DE_P$, and wherein the channel depth is at least 80% of (and preferably is at least as great as) the peripheral depth.

Also in accordance with the present invention, there is provided prosthetic vertebral endplate comprising:
  i) an outer surface having:
    a) a peripheral portion adapted to mate with a vertebral body, and
    b) and an interior portion forming a keel having a width,
  ii) an inner surface comprising an opening forming a channel having a width, wherein the keel width is greater than the channel width.

In this condition, the keel is wide enough to accommodate at least a portion of the channel and therefore at least a portion of the core member. When the keel can accommodate the core member, the overall height of the device may be advantageously decreased.

Whereas the embodiments of the present invention disclosed thus far each possess an open-ended channel having a pair of side walls for limiting the medial-lateral translation motion of the core member, other embodiments of the present invention possess other means for limiting the medial-lateral translation motion of the core member while allowing easy A-P insertion of the core member.

Now referring to FIG. 19, there is provided an endplate 1201 having an inner surface 1203 and a projection 1205 extending therefrom. The projection runs from the anterior wall 1207 to the posterior wall 1209 of the endplate. Core member 1211 has a recess 1213 having a shape that mates with the projection 1205. Sidewalls 1215 and 1217 of the projection limit the lateral translation of the core member. The articulation surface of the endplate may be either the inner surface 1203 or the upper surface 1217 of the projection.

Expulsion of the core member of this embodiment can be prevented by any number of means. For example, after the core member is slid upon the projection locking clips can be put in place at either end of the projection. Alternatively, the upper surface of the projection can comprise at least one flexible tab that allows passage of the recess of the core member towards the inner portion of the endplate, but prevents its passage back out.

Therefore, in accordance with the present invention, there is provided an intervertebral motion disc comprising:
a) a first prosthetic vertebral endplate comprising:
i) an outer surface adapted to be attached to a first vertebral body, and
ii) an inner surface comprising a first articulation surface, and
iii) an elongated rail extending from the inner surface,
b) a core member comprising:
i) a first articulation surface, and
ii) an elongated slot for receiving the rail, wherein the first articulation surface of the core member and the first articulation surface of the first endplate are adapted to form a first articulation interface, and the elongated rail is received in the elongated slot.

Although the primary function of the guide rails on the superior and inferior prosthetic endplates is to mate with instrumentation during the surgical procedure, they are also designed to accommodate the addition of optional device components. For example, if the surgeon sought to render the device completely immobile for the first few weeks immediately following implantation, the surgeon could add a stabilizing component to the device. For example, one possible geometry for such a stabilization component would be a "U" shape that could be slid into place along the guide rails. In the preferred embodiment, the stabilization component could be made of a bioresorbable material that would provide support for a few weeks after implantation and then resorb and allow the device to restore motion to the spinal segment.

In other embodiments, the additional stabilization component can transform the motion disc into a permanent spacer that prevents motion. In this case, the component would likely be used by a surgeon in a revision case. If the patient continued to experience pain or other problems after the implantation of the artificial disc replacement device, then the surgeon may feel that it would be best to reoperate and substantially eliminate motion from the spinal segment. Since the removal of implants is often problematic, the stabilization component would provide a much-desired alternative. Rather than removing the artificial disc replacement device, the surgeon could simply slide the stabilization member into place and essentially convert the motion disc into a spacer.

Therefore, in accordance with the present invention, there is provided intervertebral spacer, comprising:
a) a first motion segment comprising:
i) an outer surface adapted to mate with a first vertebral body,
ii) an inner surface comprising a motion surface, and
iii) a body portion therebetween having an anterior portion and a posterior portion,
and
b) a second motion segment comprising:
i) an outer surface adapted to mate with a second vertebral body,
ii) an inner surface comprising a motion surface, and
iii) a body portion therebetween having an anterior portion and a posterior portion, and
c) a spacing component having a first surface and an opposing second surface,
wherein the motion surfaces are adapted to form a motion interface, and
wherein the spacing component is disposed between the inner surfaces of the motion segments to substantially prevent motion at the motion interface.

In some embodiments, the spacing component is substantially U-shaped. Preferably, the substantially U-shaped spacing component has first and second end portions disposed substantially parallel to each other. In some embodiments, the first end of the spacing component is oriented substantially in the anterior-posterior direction, while in others, the first end of the spacing component is oriented at a substantial angle from the anterior-posterior direction. Preferably, this spacing component is adapted to be inserted from the anterior direction.

In some embodiments adapted to be inserted from the posterior direction, the spacing component comprises first and second independent bodies.

In some embodiments, the spacing component comprises a biologic enhancement selected from the group consisting of osteoinductive materials, osteoconductive materials, and osteogenic materials.

In some embodiments, the spacing component comprises stem cells.

The present invention is designed such that the implantation of the device can be accomplished in a straightforward manner with a minimum of distraction. The guides are designed such that the superior and inferior prosthetic vertebral endplates can be placed on an instrument that will hold them very close together without allowing the articulation surfaces to touch. The prosthetic vertebral endplates can then be inserted into the disc space in this position. This allows the surgeon to insert these components without having to significantly overdistract the disc space. The instrument can then separate the prosthetic vertebral endplates and securely force them against their respective natural vertebral endplates. At this point, a sizing tool can be used to determine the ideal height of the disc space and the appropriately sized core member can be selected. The core member is then slid into place within the retaining channel and the instrument is removed. The surgeon can then perform a final check of the placement and sizing of the device. If the surgeon is satisfied, the locking tab is secured in place.

In preferred embodiments, the disc can be inserted modularly into the disc space, wherein the endplates are first inserted (either at the same time or consecutively) and then the core member is inserted. Because the distance separating the endplates at the periphery of the disc exceeds the height of a concave core member, the core member may be inserted between the prosthetic endplates without excessive overdistraction of the disc space.

Therefore, in accordance with the present invention, there is provided a intervertebral motion disc comprising:
  a) a first prosthetic vertebral endplate comprising:
    i) an outer surface adapted to be attached to a first vertebral body,
    ii) an inner surface comprising an inner portion and a peripheral portion,
      wherein at least one of the portions comprises a first articulation surface, and
  b) a second prosthetic vertebral endplate comprising:
    i) an outer surface adapted to be attached to a second vertebral body,
    ii) an inner surface comprising an inner portion and a peripheral portion,
      wherein at least one of the portions comprises a first articulation surface,
  c) a core member comprising:
    i) a first articulation surface adapted for articulation with the first articulation surface of the first endplate, and
    ii) a second articulation surface adapted for articulation with the first articulation surface of the second endplate, and
  d) means for limiting the translation motion of the core member,
wherein the core member is disposed between the endplates and oriented therein to produce a first articulation interface between the first articulation surface of the first endplate and the first articulation surface of the core member, and a second articulation interface between the first articulation surface of the second endplate and the second articulation surface of the core member, and a distance between the peripheral portions of the first and second endplates, and wherein the distance between the peripheral portions is greater than the height of the core member.

Because the motion disc of the present invention will substantially mimic the motion of the natural interverterbal disc, there may be times in which the spine hyperextends to create an extreme lordotic posture. In these situations, the distance between the anterior portions of the prosthetic vertebral endplates may become unacceptably large. In order to limit the extent of lordotic hyperextension, in some embodiments, a ligament is attached between the anterior portions of the endplates.

Therefore, in accordance with the present invention, there is provided an intervertebral motion disc comprising:
  a) a first motion segment comprising:
    i) an outer surface adapted to mate with a first vertebral body,
    ii) an inner surface comprising a motion surface, and
    iii) a body portion therebetween having an anterior portion and a posterior portion,
  b) a second motion segment comprising:
    i) an outer surface adapted to mate with a second vertebral body,
    ii) an inner surface comprising a motion surface, and
    iii) a body portion therebetween having an anterior portion and a posterior portion, and
  c) a ligament having a first end and a second end,
wherein the motion surfaces are adapted to form a motion interface, and
wherein the first end of the ligament is connected to the anterior portion of the first motion segment and the second end of the ligament is connected to the anterior portion of the second motion segment.

Preferably, the ligament comprises a biocompatible flexible material. More preferably, the biocompatible flexible material is selected from the group consisting of:
  i) a polyester fiber weave,
  ii) an elastic material (such as silicon, polyurethane, and natural rubber),
  iii) a polyvinyl material, and
  iv) a biological material capable of forming a scaffold for natural regeneration of a resected ligament, such as small intestinal submucosa SIS.

Although the present invention has been described with reference to its preferred embodiments, those skillful in the art will recognize changes that may be made in form and structure which do not depart from the spirit of the invention.

Figure 20B:
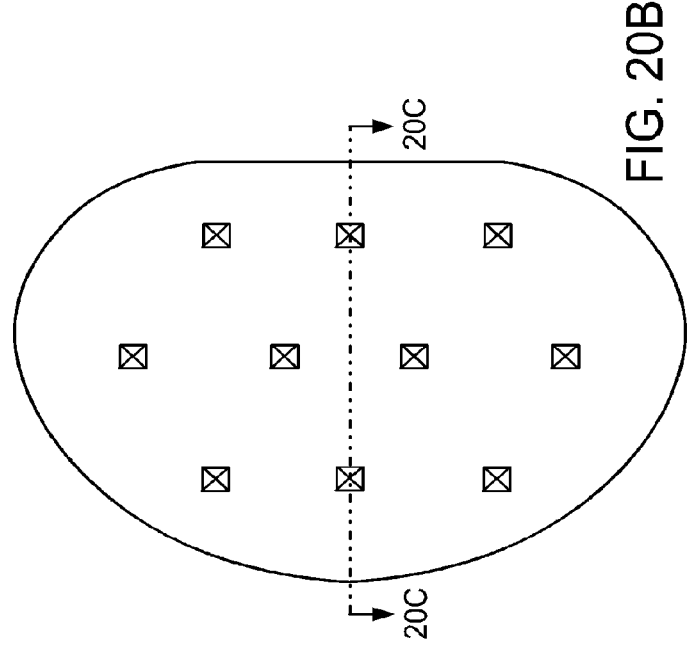
FIGS. 20a-20c disclose isometric, elevated, and cross-sectional views of an embodiment of the present invention in which the core member has a significantly convex articulation surface and a substantially flat articulation surface.
Figure 20C:
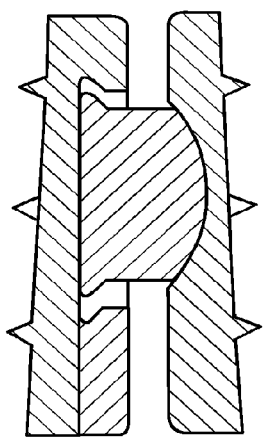
Figure 20A:
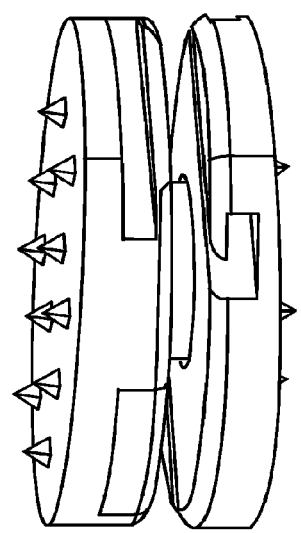
Figure 25:
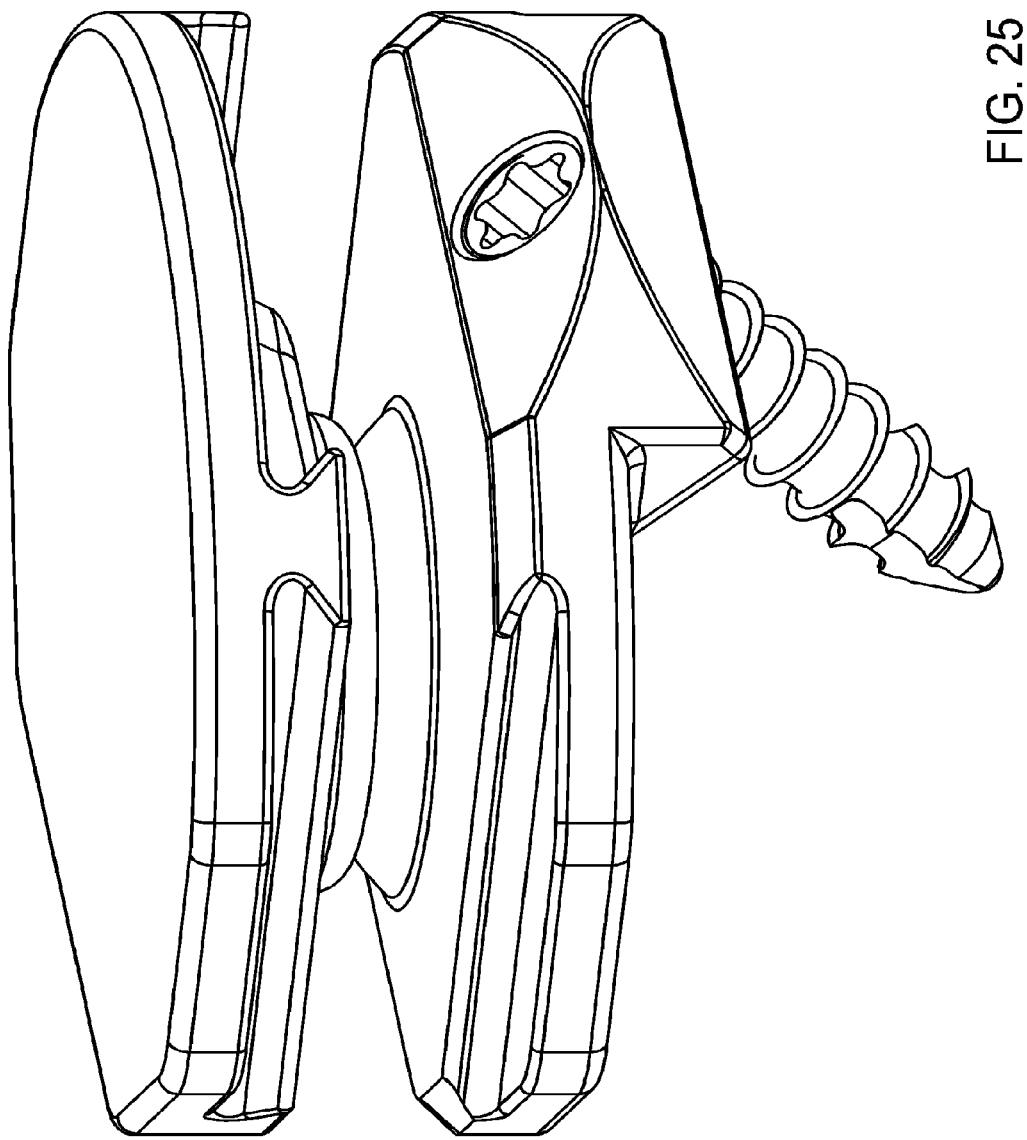
FIG. 25 discloses an isometric view of the present invention in which one endplate is adapted to receive a screw for fixation to an adjacent vertebra.

For example, any of the devices disclosed in the FIGS. may be rotated 180 degrees such that the inferior and superior endplates swap places. In addition, the articulation surfaces of the core member could be made either concave or convex. For example, FIGS. 20a-20c provides one such alternative embodiment wherein the core member has a convex articulation surface. Moreover, additional components could be added to the device to enhance the design such as screws through the endplates to provide for improved fixation as shown in FIG. 25.

Figure 21B:
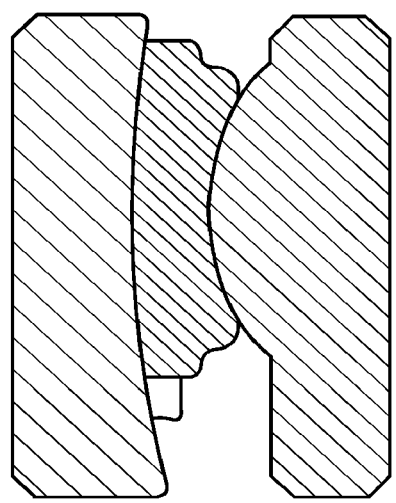
FIGS. 21a-21b discloses a front and a cross-sectional view of another embodiment of the present invention having a slightly curved articulation interface running the anterior-posterior direction.
Figure 21A:
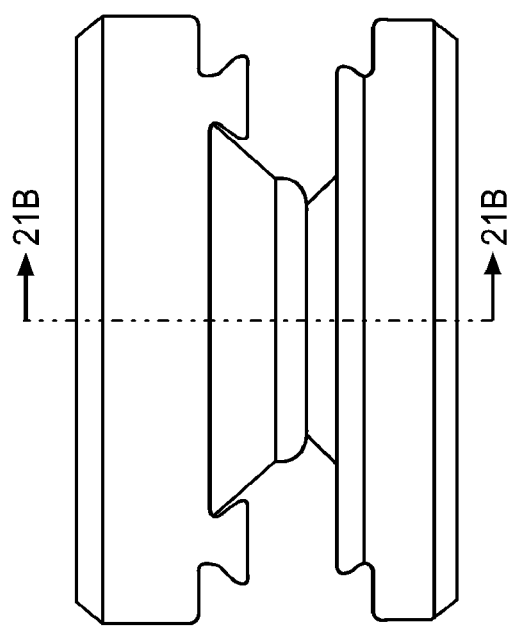

Now referring to FIGS. 21a and 21b, there is provided an alternative embodiment of the present invention. The intervertebral motion disc of FIGS. 21a-21b is substantially similar to the motion disc of FIGS. 1a-1c, with the following modifications:

First, the relative size of the core member in FIGS. 21a and 21b is substantially larger than that of the core member in FIGS. 1a-1c and is preferably made of a polymeric material such as polyethylene.

Second, the second articulation interface formed by the core member and the upper endplate is slightly curved and hemicylindrical. The slight curve of the hemicylinder is oriented in the A-P direction (as shown in FIG. 21b), while the linear dimension thereof is oriented in the M-L direction (as shown in FIG. 21a). The articulation interfaces are oriented in the same direction.

Figure 22B:
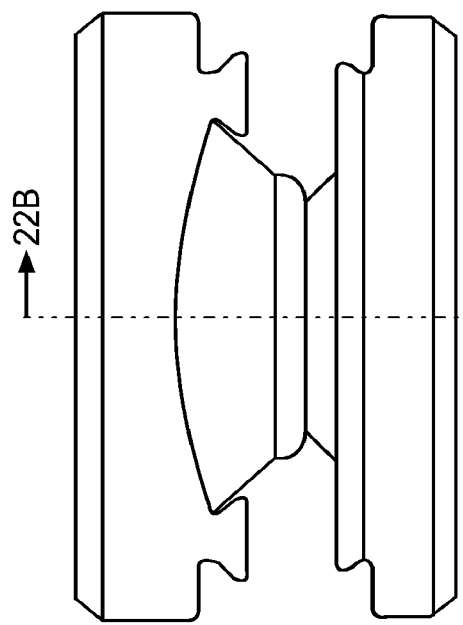
FIGS. 22a-22b discloses a front and a cross-sectional view of another embodiment of the present invention having a slightly curved articulation interface running the medial-lateral direction.
Figure 22A:
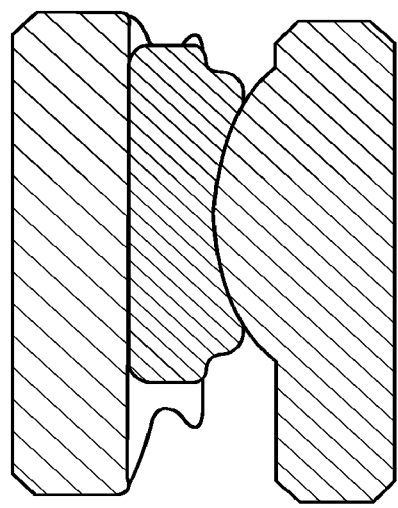

Now referring to FIGS. 22a and 22b, there is provided a motion disc substantially similar to that shown in FIGS. 21a and 21b, except that the slight curve of the hemicylinder is oriented in the M-L direction (as shown in FIG. 22a), while the linear dimension thereof is oriented in the A-P direction (as shown in FIG. 22b).

Figure 23:
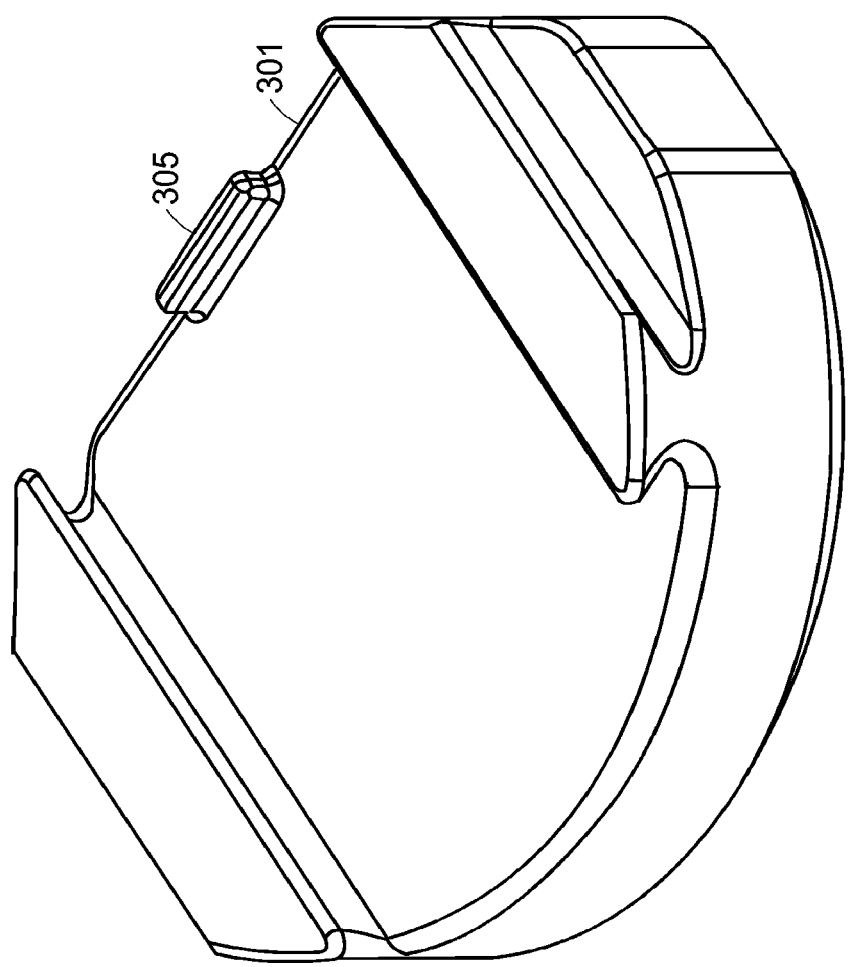
FIG. 23 discloses an isometric view of a prosthetic vertebral endplate of the present invention having a channel having two open ends.

Now referring to FIG. 23, there is provided an endplate for a motion disc wherein the sidewall of the endplate comprises a third opening 301 in communication with the first opening in the sidewall and the second opening in the inner surface, so that the channel formed thereby is substantially open at each of its ends. A small lip 305 rises from the bottom surface of the posterior end of the channel and functions to keep the core from sliding out the posterior end of the channel.

Figure 24:
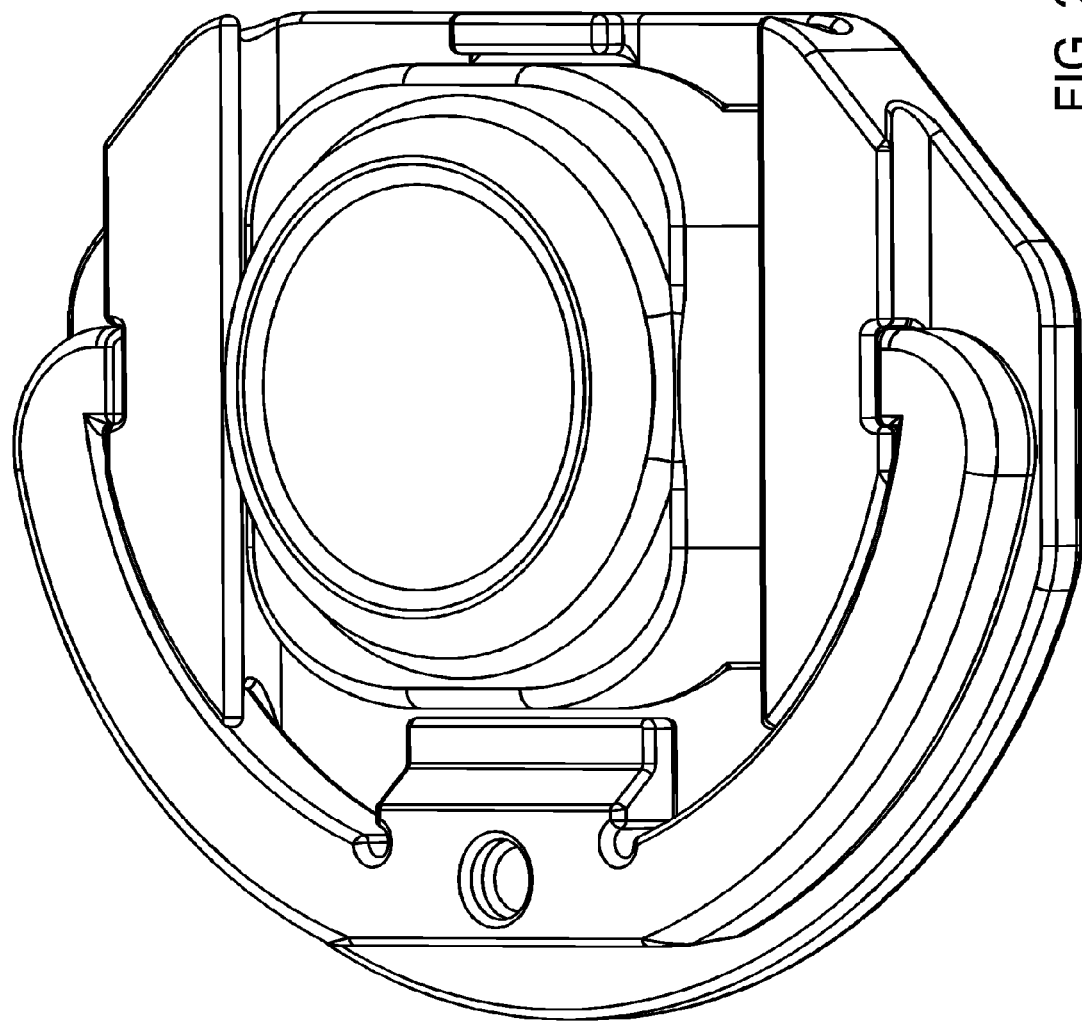
FIG. 24 discloses an isometric view of the present invention in which a locking tab comprises first and second arms, and each arm is shaped to be secured to the endplate in a recess formed in the lateral wall portions of the endplate.

Now referring to FIG. 24, there is provided another embodiment of the present invention in which the means comprises a locking tab comprising first and second arms, the endplate further comprises first and second lateral wall portions comprising first and second respective recesses, wherein the first arm is shaped to be secured to the endplate in the first recess, and the second arm is shaped to be secured to the endplate in the second recess. In this FIG. 24, the tab is secured in place.

Now referring to FIG. 25, there is provided another embodiment of the present invention in which one endplate is adapted to receive a screw for fixation to an adjacent vertebra. In this FIG. 25, the screw is received within the through-hole.

Figure 26A:
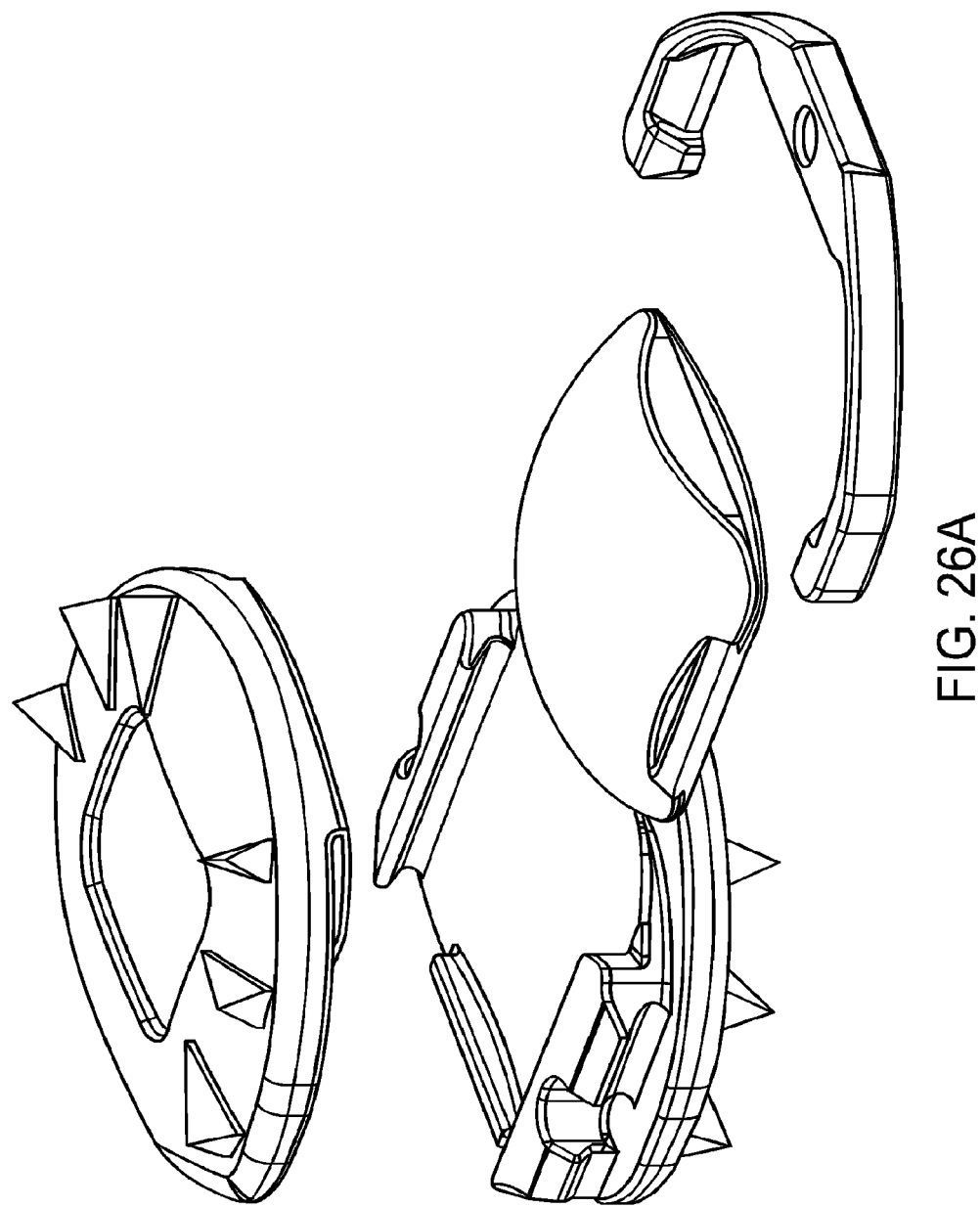
FIGS. 26a and 26b disclose exploded views of an embodiment of the invention.
Figure 26B:
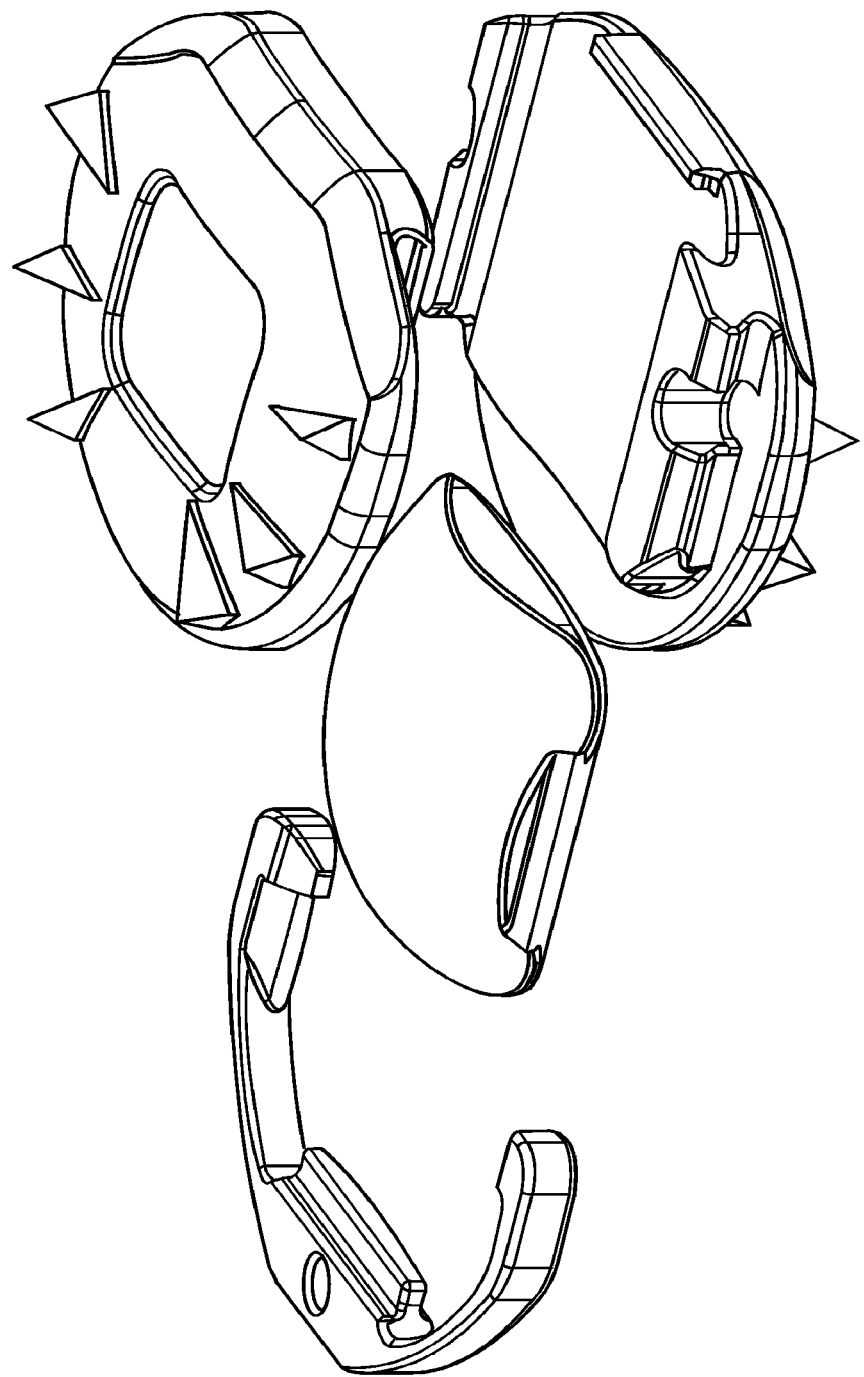

Now referring to FIGS. 26a and 26b, there is provided an alternative embodiment of the present invention. The intervertebral motion disc of FIGS. 26a and 26b is substantially similar to the motion discs described above, with the following modifications: First, the endplate fins are now located more laterally on the outer surfaces of the prosthetic endplates in order to better resist lateral migration. Second, a more substantial radius has been provided on the posterior edges of the outer surfaces of the prosthetic endplates in order to provide a better anatomical fit with the natural endplate. Third, the core material is made of a standard, non-cross-linked ultrahigh molecular weight polyethylene. In addition, the core component may include tantalum markers for x-ray visualization. Fourth, the prosthetic endplates are made of a standard CoCr material. Fifth, the central portions of the outer surfaces of the prosthetic endplates each have a recessed portion for providing a better fixation. In other embodiments, the central recessed portion is removed and the entire outer surfaces of the endplates are coated with an HA-based coating.

Figure 27:
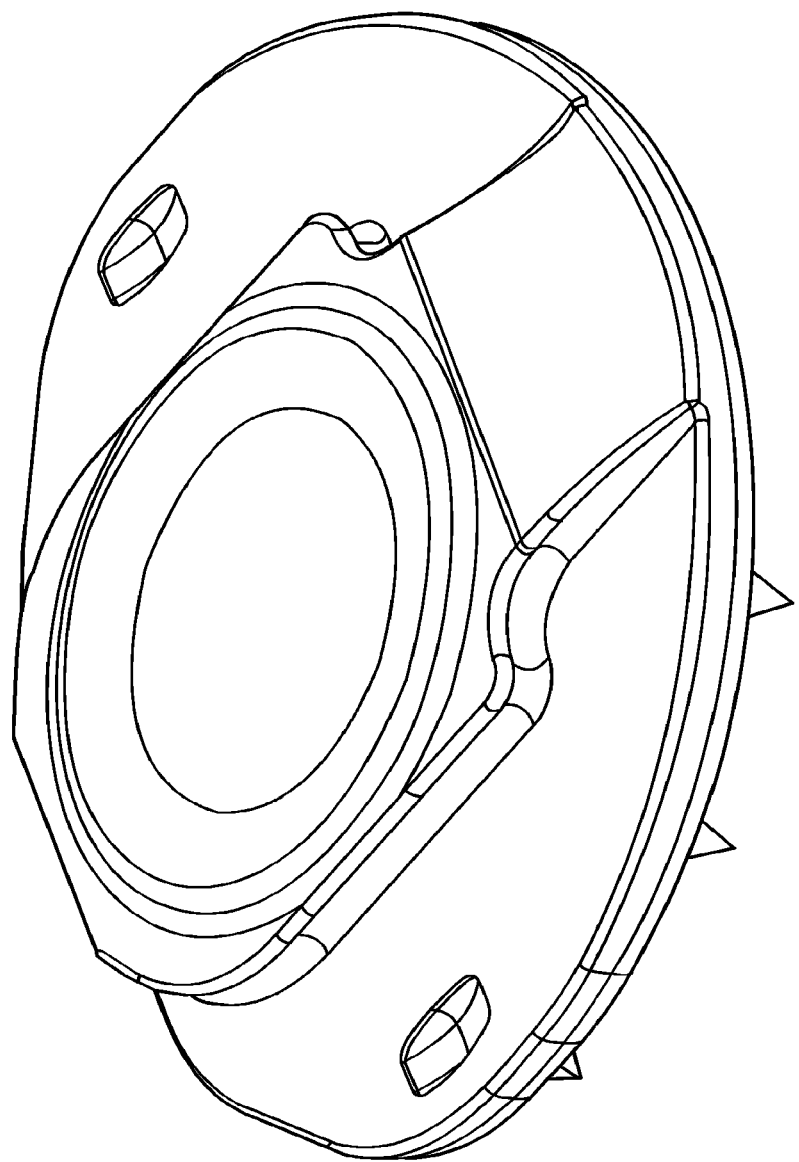
FIG. 27 discloses a notched endplate of the present invention.

FIG. 27 discloses an isometric view of a superior endplate of the present invention having a pair of notches on its inner surface for mating with an insertion instrument.

What is claimed:

1. An intervertebral device comprising:
a first polymeric component having a first bearing surface and a second bearing surface opposite the first bearing surface, the second bearing surface having teeth configured to mate with a vertebral body wherein the first polymeric component comprises PEEK; and
a porous titanium coating that coats the first bearing surface wherein the first polymeric component further comprises a tapered projection that extends out from the first bearing surface in a direction away from the second bearing surface.

2. The intervertebral device of claim 1, wherein the porous titanium coating has a material property of promoting bony affixation.

3. The intervertebral device of claim 2, wherein the coating comprises pores having an average pore size of 250 microns.

4. The intervertebral device of claim 1, wherein the first polymeric component comprises a plurality of tapered surfaces that extend out from the first bearing surface in a direction away from the second bearing surface.

5. The intervertebral device of claim 4, wherein the tapered surfaces are spaced from each other so as to define a gap therebetween.

6. An intervertebral device comprising a polymeric endplate component having a first bone-facing surface that is toothed to promote vertebral fixation in an intervertebral space, and a second surface opposite the first bone-facing surface, wherein the second surface is coated with a porous coating of titanium, wherein the polymeric endplate component comprises PEEK, and wherein the polymeric endplate component further comprises a plurality of projections that extend out from the second surface in a direction away from the first bone-facing surface.

7. The intervertebral device of claim 6, wherein the porous coating of titanium has a material property of promoting bony affixation.

8. The intervertebral device of claim 7, wherein the porous coating of titanium comprises pores having an average pore size of 250 microns.

9. The intervertebral device of claim 6, wherein the plurality of projections includes a plurality of tapered surfaces that extend out from the second surface away from the first bone-facing surface.

10. The intervertebral device of claim 9, wherein the tapered surfaces are spaced from each other so as to define a gap therebetween.

11. The intervertebral device of claim 6, wherein the plurality of projections includes a tapered projection.

* * * * *